(12) United States Patent
van der Burg et al.

(10) Patent No.: US 8,663,646 B2
(45) Date of Patent: Mar. 4, 2014

(54) P53 PEPTIDE VACCINE

(75) Inventors: Sjoerd Henricus van der Burg, Leiden (NL); Rienk Offringa, Leiden (NL); Cornelis Johannes Maria Melief, Haarlem (NL); Gemma G. Kenter, Amsterdam (NL)

(73) Assignee: Academisch Ziekenhuis Leiden h.o.d.n. LUMC, ZA Leiden (NL)

( * ) Notice: Subject to any disclaimer, the term of this patent is extended or adjusted under 35 U.S.C. 154(b) by 192 days.

(21) Appl. No.: 12/592,815

(22) Filed: Dec. 3, 2009

(65) Prior Publication Data

US 2010/0210529 A1   Aug. 19, 2010

Related U.S. Application Data

(63) Continuation of application No. PCT/NL2008/050319, filed on May 27, 2008.

(60) Provisional application No. 60/941,070, filed on May 31, 2007, provisional application No. 60/942,483, filed on Jun. 7, 2007.

(30) Foreign Application Priority Data

May 31, 2007   (EP) .................................... 07109287
Jun. 7, 2007   (EP) .................................... 07109802

(51) Int. Cl.
*A61K 39/00* (2006.01)
*A61K 45/00* (2006.01)
*A61K 38/16* (2006.01)

(52) U.S. Cl.
USPC .................. 424/185.1; 424/277.1; 424/278.1

(58) Field of Classification Search
None
See application file for complete search history.

(56) References Cited

U.S. PATENT DOCUMENTS

2003/0194704 A1* 10/2003 Penn et al. .................. 435/6

FOREIGN PATENT DOCUMENTS

WO   WO-01/09325   2/2001

OTHER PUBLICATIONS

Fournier and Schirrmacher (Expert. Rev. Vaccines 8(1); 51-66, 2009, see entire reference).*
Schrieber et al (Seminar. Immunol. 22: 105-112, 2010, see entire reference).*
Klebanoff et al (Immunol. Rev. 2011, 239: 27-44, see entire reference).*
Geneseq ABO56177, Jul. 2004.*
Fairchild P J et al: "Lowering the tone: mechanisms of immunodominance among epitopes with low affinity for MHC" Immunology Today, Elsevier Publications, Cambridge, GB, vol. 17, No. 2, Feb. 1, 1996, pp. 80-85.
Castelli C et al: "Mass spectrometric identification of a naturally processed melanomapeptide recognized by CD8+ cytotoxic t lymphocytes" Journal of Experimental Medicine, Rockefeller University Press, JP, vol. 181, No. 1, Jan. 1, 1995 pp. 363-368.
Nijman H W et al: "Characterization of cytotoxic T Lymphocyte epitopes of a self-protein, P53, and a non-self-protein, influenza matrix: relationship between major histocompatibility complex peptide binding affinity and immune responsiveness to peptides" Journal of Immunotherapy, Lippincott Williams and Wilkins, Hagerstown, MD, US, vol. 14, No. 2, Jan. 1, 1993, pp. 121-126.
Cox A L et al: "Identification of a peptide recognized by five melanoma-specific human cytotoxic T cell lines" Science, American Association for the Advancement of Science, US, Washington, DC, vol. 264, No. 5159, Apr. 29, 1994, pp. 716-719.
Van Hall T et al: "Selective cytotoxic T-lymphocyte targeting of tumor immune escape variants" Nature Medicine, Nature Publishing Group, New York, NY US, vol. 12, No. 4, Jan. 1, 2006, pp. 417-424.
Lambeck Annechien et al: "P53-specific T cell responses in patients with malignant and benign ovarian tumors: implications for P53 based immunotherapy" International Journal of Cancer, John Wiley & Sons, Inc., United States, Switzerland Germany, vol. 121, No. 3, Jan. 1, 2007, pp. 606-614.
Morgan D J et al: "Activation of low avidity CTL specific for a self epitope results in tumor rejection but not autoimmunity" Journal of Immunology, American Association of Immunologists, US, vol. 160, No. 2, Jan. 15, 1998, pp. 643-651.
Selivanova G et al: "Restoration of the growth suppression function of mutant P53 by a synthetic peptide derived from the P53 c-terminal domain" Nature Medicine, Nature Publishing Group, New York, NY, US, vol. 3, No. 6, Jun. 1, 1997, pp. 632-638.
Visser De K E et al: "Tracing and characterization of the low-avidity self-specific T cell repertoire" European Journal of Immunology, Wiley-V C H Verlag GMBH and Co. Kgaa, DE, vol. 30, No. 5, May 1, 2000, pp. 1458-1468.
Li Yin et al: "Selective induction of apoptosis through the FADD/caspase-8 pathway by a P53 c-terminal peptide in human pre-malignant and malignant cells" International Journal of Cancer, John Wiley & Sons, Inc., United States, Switzerland, Germany, vol. 115, No. 1, May 20, 2005, pp. 55-64.
Michl Josef et al: "PNC-28, a P53-derived peptide that is cytotoxic to cancer cells, blocks pancreatic cancer cell growth in vivo" International Journal of Cancer, John Wiley and Sons, Inc., United States, Switzerland, Germany, vol. 119, No. 7, Oct. 1, 2006, pp. 1577-1585.
Lomas M et al: "Phase I clinical trial of a human idiotypic P53 vaccine in patients with advanced malignancy" Annals of Oncology, Kluwer, Dordrecht, vol. 15, No. 2, Feb. 1, 2004, pp. 324-329.
Nijman HW et al: "Immunologic aspect of ovarian cancer and P53 as tumor antigen" Journal of Translational Medicine, Biomed Central, London, GB, vol. 3, No. 1, Sep. 15, 2005, p. 34.
Klinguer-Hamour Christine et al: "DDA adjuvant induces a mixed Th1/Th2 immune response when associated with BBG2Na, a respiriatory syncytial virus potential vaccine" Vaccine Jun. 21, 2002, vol. 20, No. 21-22, pp. 2743-2751.
International Search Report re: PCT/NL2008/050319 dated Oct. 7, 2008.

(Continued)

*Primary Examiner* — Gerald R Ewoldt
*Assistant Examiner* — Marianne Dibrino
(74) *Attorney, Agent, or Firm* — Sunstein Kann Murphy & Timbers LLP

(57) ABSTRACT

The invention relates to a peptide derived from p53 that could be used as a vaccine against cancer.

5 Claims, 18 Drawing Sheets

(56) References Cited

OTHER PUBLICATIONS

Barfoed et al., "Cytotoxic T-lymphocyte clones, established by stimulation with the HLA-A2 binding p5365-73 wild type peptide loaded on dendritic cells In vitro, specifically recognize and lyse HLA-A2 tumour cells overexpressing the p53 protein", *Scand J Immunol.* 51: 128-33, 2000.

Eura et al., "A wild-type sequence p53 peptide presented by HLA-A24 induces cytotoxic T lymphocytes that recognize squamous cell carcinomas of the head and neck", *Clin Cancer Res.* 6: 979-86., 2000.

Hernandez et al., "The use of HLA A2.1/p53 peptide tetramers to visualize the impact of self tolerance on the TCR repertoire [In Process Citation]", *J Immunol.* 164: 596-602, 2000.

Houbiers et al., "In vitro induction of human cytotoxic T lymphocyte responses against peptides of mutant and wild-type p53", *Eur J Immunol.* 23: 2072-7, 1993.

Mayordomo et al., "Therapy of murine tumors with p53 wild-type and mutant sequence peptide-based vaccines", *J Exp Med.* 183: 1357-65, 1996.

Ropke et al., "Spontaneous human squamous cell carcinomas are killed by a human cytotoxic T lymphocyte clone recognizing a wild-type p53-derived peptide", *Proc Natl Acad Sci U S A.* 93: 14704-7, 1996.

Theobald et al., "The sequence alteration associated with a mutational hotspot in p53 protects cells from lysis by cytotoxic T lymphocytes specific for a flanking peptide epitope", *J Exp Med.* 188: 1017-28, 1998.

van der Burg et al., "Immunogenicity of peptides bound to MHC class I molecules depends on the MHC-peptide complex stability", *J Immunol.* 156: 3308-14, 1996.

van der Burg et al., "Long lasting p53-specific T cell memory responses in the absence of anti-p53 antibodies in patients with resected primary colorectal cancer", *Eur J Immunol.* 31: 146-55., 2001.

\* cited by examiner

Fig 1
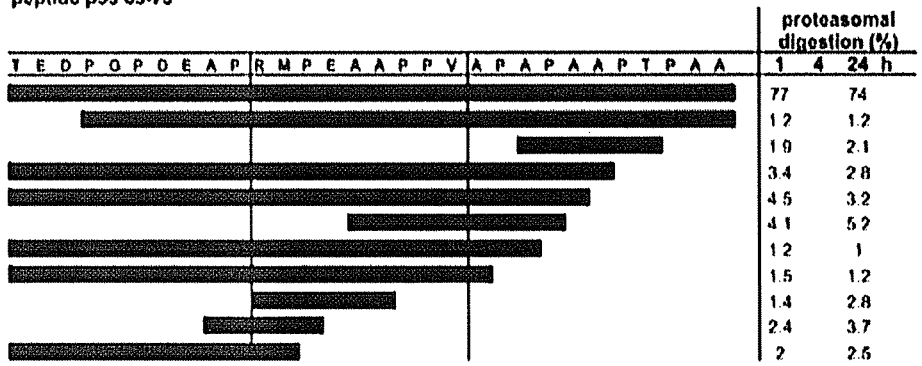
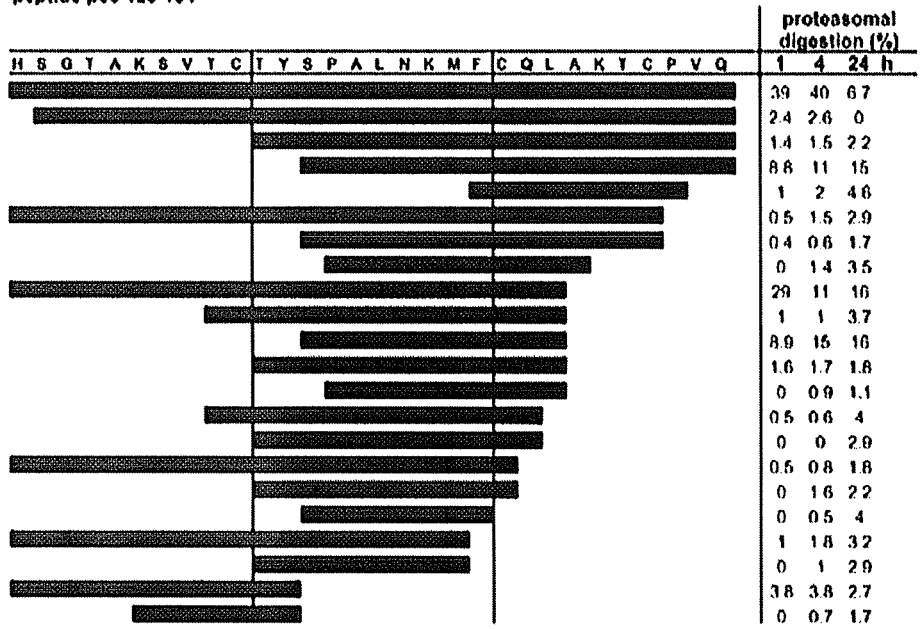
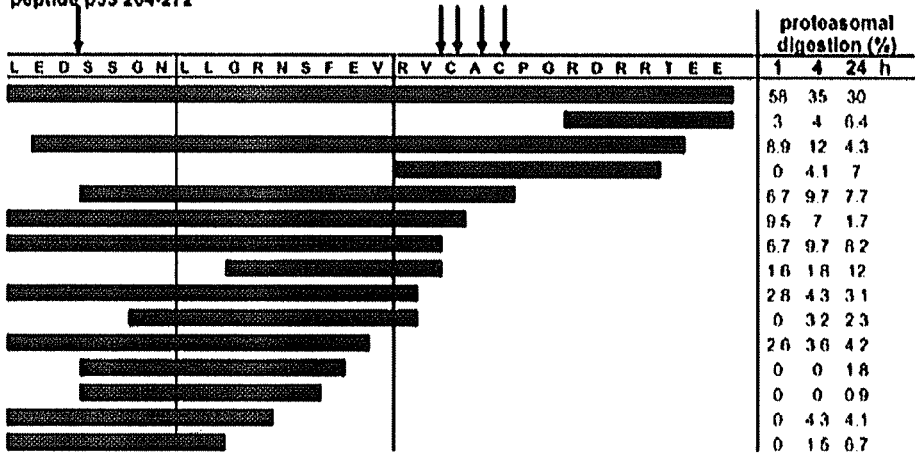

Flow chart phase I (5 patients) – II (14 patients) vaccination study.

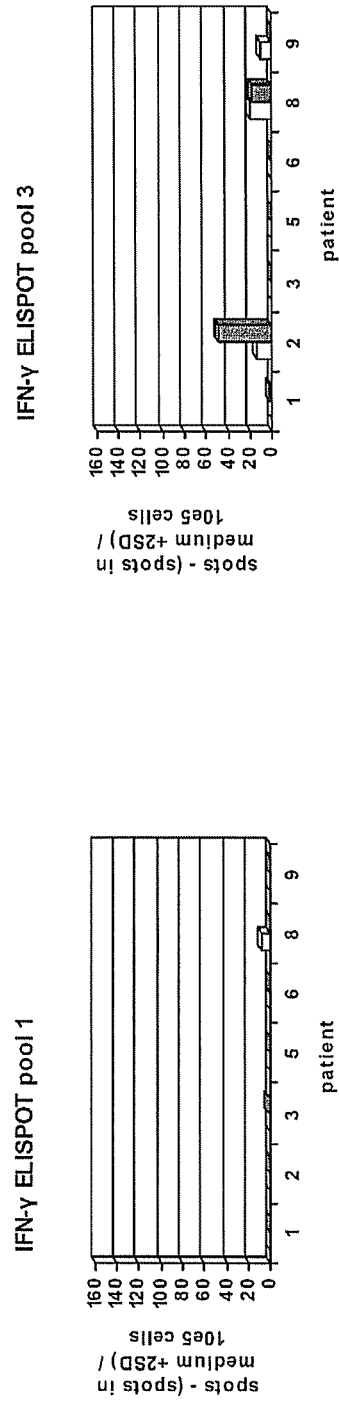

Responses to individual peptides

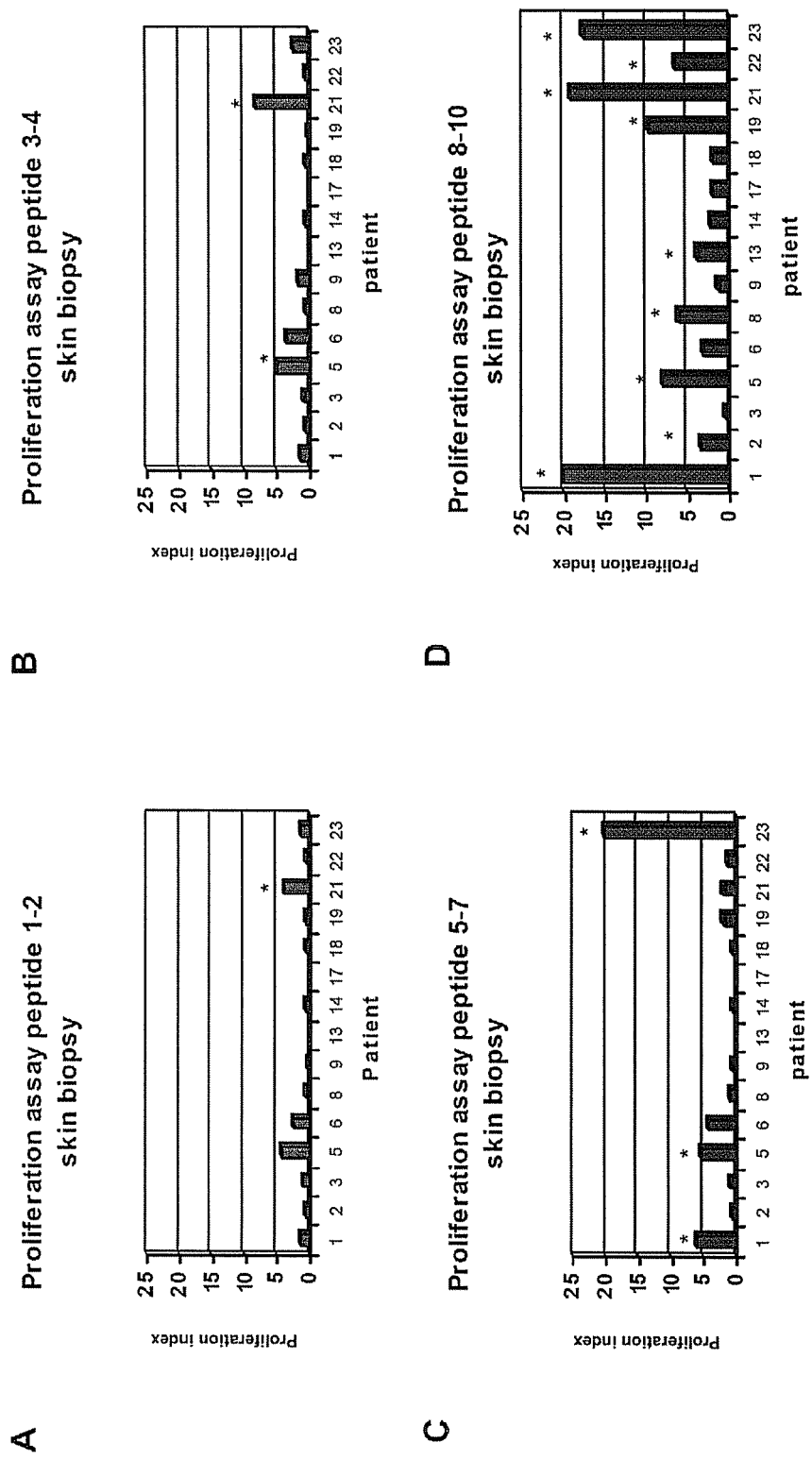

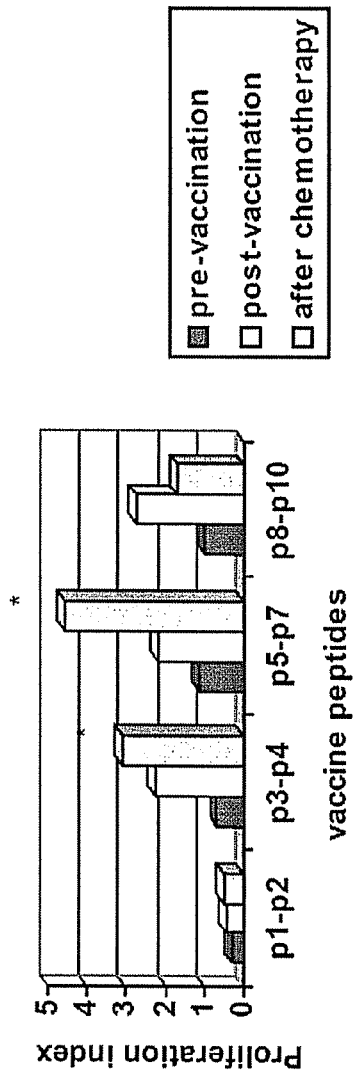
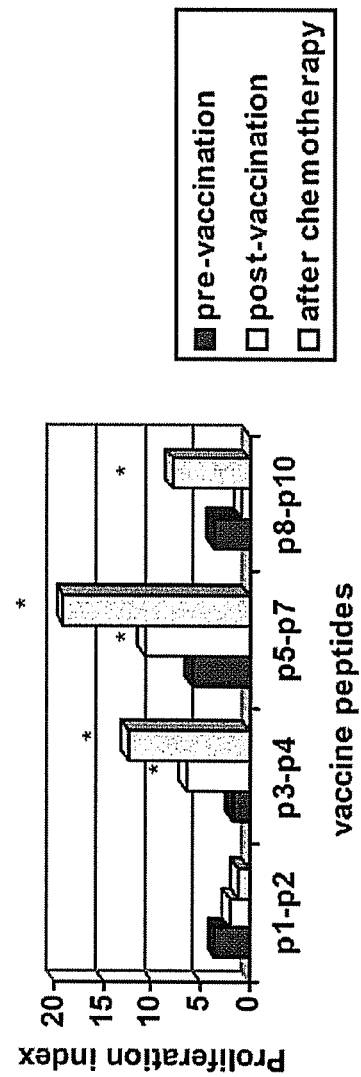
Fig 12

SEQUENCE LISTING

```
<160> NUMBER OF SEQ ID NOS: 93

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
```

```
                290                 295                 300
Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
                355                 360                 365

Leu Lys Ser Lys Lys Gly Gln Ser Thr Ser Arg His Lys Lys Leu Met
                370                 375                 380

Phe Lys Thr Glu Gly Pro Asp Ser Asp
385                 390

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Pro Ala Pro Ser Trp Pro Leu Ser Ser Val Pro Ser Gln Lys
1               5                   10                  15

Thr Tyr Gln Gly Ser Tyr Gly Phe Arg Leu Gly Phe Leu His
                20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Thr Tyr Gln Gly Ser Tyr Gly Phe Arg Leu Gly Phe Leu His Ser Gly
1               5                   10                  15

Thr Ala Lys Ser Val Thr Cys Thr Tyr Ser Pro Ala Leu Asn
                20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      primer

<400> SEQUENCE: 4

Pro Val Gln Leu Trp Val Asp Ser Thr Pro Pro Pro Gly Thr Arg Val
1               5                   10                  15

Arg Ala Met Ala Ile Tyr Lys Gln Ser Gln His Met Thr Glu
                20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 5

Val Arg Ala Met Ala Ile Tyr Lys Gln Ser Gln His Met Thr Glu Val
1               5                   10                  15

Val Arg Arg Cys Pro His His Glu Arg Cys Ser Asp Ser Asp
                20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Pro Pro Gln His Leu Ile Arg Val Glu Gly Asn Leu Arg Val Glu Tyr
1               5                   10                  15

Leu Asp Asp Arg Asn Thr Phe Arg His Ser Val Val Val Pro
                20                  25                  30

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Val Gly Ser Asp Cys Thr Thr Ile His Tyr Asn Tyr Met Cys Asn
1               5                   10                  15

Ser Ser Cys Met Gly Gly Met Asn Arg
                20                  25

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Val Gly Ser Asp Cys Thr Thr Ile His Tyr Asn Tyr Met Cys Asn Ser
1               5                   10                  15

Ser Cys Met Gly Gly Met Asn Arg Arg Pro Ile Leu Thr Ile
                20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Glu Asp Ser Ser Gly Asn Leu Leu Gly Arg Asn Ser Phe Glu Val
1               5                   10                  15

Arg Val Cys Ala Cys Pro Gly Arg Asp Arg Arg Thr Glu Glu
                20                  25                  30

<210> SEQ ID NO 10
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 10

Arg Val Cys Ala Cys Pro Gly Arg Asp Arg Arg Thr Glu Glu Glu Asn
1               5                   10                  15

Leu Arg Lys Lys Gly Glu Pro His His Glu Leu Pro Pro Gly
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Lys Arg Ala Leu Pro Asn Asn Thr Ser Ser Ser Pro Gln Pro Lys Lys
1               5                   10                  15

Lys Pro Leu Asp Gly Glu Tyr Phe Thr Leu Gln Ile Arg Gly
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Gln Ala Gly Lys Glu Pro Gly Gly Ser Arg Ala His Ser Ser His
1               5                   10                  15

Leu Lys Ser Lys Lys Gly Gln Ser Thr Ser Arg His Lys Lys
            20                  25                  30

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Lys Ser Lys Lys Gly Gln Ser Thr Ser Arg His Lys Lys Leu Met
1               5                   10                  15

Phe Lys Thr Glu Gly Pro Asp Ser Asp
            20                  25

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Asp Asp Arg Asn Thr Phe Arg His Ser Val Val Val Pro Tyr Glu
1               5                   10                  15

Pro Pro Glu Val Gly Ser Asp Cys Thr Thr Ile His Tyr Asn
            20                  25                  30
```

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Arg Arg Cys Pro His His Glu Arg Cys Ser Asp Ser Asp Gly Leu Ala
1               5                   10                  15

Pro Pro Gln His Leu Ile Arg Val Glu Gly Asn Leu Arg Val
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Cys Met Gly Gly Met Asn Arg Arg Pro Ile Leu Thr Ile Ile Thr
1               5                   10                  15

Leu Glu Asp Ser Ser Gly Asn Leu Leu Gly Arg Asn Ser Phe
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Arg Lys Lys Gly Glu Pro His His Glu Leu Pro Pro Gly Ser Thr
1               5                   10                  15

Lys Arg Ala Leu Pro Asn Asn Thr Ser Ser Ser Pro Gln Pro
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Lys Pro Leu Asp Gly Glu Tyr Phe Thr Leu Gln Ile Arg Gly Arg Glu
1               5                   10                  15

Arg Phe Glu Met Phe Arg Glu Leu Asn Glu Ala Leu Glu Leu
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
-continued

Arg Phe Glu Met Phe Arg Glu Leu Asn Glu Ala Leu Glu Leu Lys Asp
1               5                   10                  15

Ala Gln Ala Gly Lys Glu Pro Gly Gly Ser Arg Ala His Ser
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Tyr Ser Pro Ala Leu Asn Lys Met Phe Cys Gln Leu Ala Lys Thr Cys
1               5                   10                  15

Pro Val Gln Leu Trp Val Asp Ser Thr Pro Pro Gly Thr
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Pro Pro Val Ala Pro Ala Pro Ala Ala Pro Thr Pro Ala Ala Pro
1               5                   10                  15

Ala Pro Ala Pro Ser Trp Pro Leu Ser Ser Ser Val Pro Ser
            20                  25                  30

<210> SEQ ID NO 22
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160
```

```
His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
        355                 360                 365

<210> SEQ ID NO 23
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```

```
<210> SEQ ID NO 24
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Thr Ala Lys Ser Val Thr Cys Thr Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Val Glu Gly Asn Leu Arg Val Glu Tyr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Leu Asp Asp Arg Asn Thr Phe Arg His
1               5                   10

<210> SEQ ID NO 28
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 28

Gly Ser Asp Cys Thr Thr Ile His Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Thr Thr Ile His Tyr Asn Tyr
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Leu Leu Pro Glu Asn Asn Val Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Met Pro Glu Ala Ala Pro Pro Val
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Leu His Ser Gly Thr Ala Lys Ser Val
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Thr Pro Pro Pro Gly Thr Arg Val
1               5

<210> SEQ ID NO 34
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Leu Ala Pro Pro Gln His Leu Ile Arg Val
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Leu Gly Arg Asn Ser Phe Glu Val
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Leu Asp Gly Glu Tyr Phe Thr Leu
1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Thr Tyr Gln Gly Ser Tyr Gly Phe Arg
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Leu Gly Phe Leu His Ser Gly Thr Ala Lys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Gly Phe Leu His Ser Gly Thr Ala Lys
```

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Phe Leu His Ser Gly Thr Ala Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Leu His Ser Gly Thr Ala Lys
1               5

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Thr Ala Lys Ser Val Thr Cys Thr Tyr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Val Thr Cys Thr Tyr Ser Pro Ala Leu Asn Lys
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Thr Tyr Ser Pro Ala Leu Asn Lys
1               5

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Ala Leu Asn Lys Met Phe Cys Gln Leu Ala Lys
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Met Phe Cys Gln Leu Ala Lys
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Thr Arg Val Arg Ala Met Ala Ile Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Thr Arg Val Arg Ala Met Ala Ile Tyr Lys
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Val Arg Ala Met Ala Ile Tyr
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Val Arg Ala Met Ala Ile Tyr Lys
1               5

<210> SEQ ID NO 51
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 51

Val Val Arg Arg Cys Pro His His Glu Arg
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gly Ser Arg Ala His Ser Ser His Leu Lys
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Arg Ala His Ser Ser His Leu Lys
1               5                   10

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala His Ser Ser His Leu Lys
1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ala His Ser Ser His Leu Lys Ser Lys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ala His Ser Ser His Leu Lys Ser Lys Lys
1               5                   10
```

```
<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Gly Gln Ser Thr Ser Arg His Lys
1               5

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Thr Ser Arg His Lys Lys Leu Met Phe Lys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Thr Tyr Gln Gly Ser Tyr Gly Phe Arg
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Gly Phe Leu His Ser Gly Thr Ala Lys
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Phe Leu His Ser Gly Thr Ala Lys
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62
```

Cys Thr Tyr Ser Pro Ala Leu Asn Lys
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Met Phe Cys Gln Leu Ala Lys
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Val Arg Ala Met Ala Ile Tyr Lys
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Asn Thr Ser Ser Ser Pro Gln Pro Lys
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asn Thr Ser Ser Ser Pro Gln Pro Lys Lys
1               5                   10

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Ser Ser Ser Pro Gln Pro Lys
1               5

<210> SEQ ID NO 68
<211> LENGTH: 9
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 68

Arg Thr Glu Glu Glu Asn Leu Arg Lys
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ala His Ser Ser His Leu Lys
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gln Ser Thr Ser Arg His Lys Lys
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Phe Ser Asp Leu Trp Lys Leu Leu
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Tyr Gln Gly Ser Tyr Gly Phe Arg Leu
1               5                   10

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Tyr Gly Phe Arg Leu Gly Phe
1               5

<210> SEQ ID NO 74

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Tyr Gly Phe Arg Leu Gly Phe Leu
1               5

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Tyr Ser Pro Ala Leu Asn Lys Met Phe
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Tyr Leu Asp Asp Arg Asn Thr Phe
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Met Phe Arg Glu Leu Asn Glu Ala Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Met Pro Glu Ala Ala Pro Pro Val
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ser Thr Pro Pro Pro Gly Thr Arg Val
```

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Leu Ala Pro Pro Gln His Leu Ile Arg Val
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Tyr Ser Pro Ala Leu Asn Lys Met Phe
1               5                   10

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Leu Gly Arg Asn Ser Phe Glu Val
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Val Leu Asp Gly Leu Asp Val Leu Leu
1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Leu Tyr Ser Phe Pro Glu Pro Glu Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Leu Tyr Val Asp Ser Leu Phe Phe Leu
1               5                   10

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Leu Leu Gln His Leu Ile Gly Leu
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Leu Glu Pro Ala Cys Ala Lys
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Lys Val Phe Pro Cys Ala Leu Ile Asn Lys
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Lys Val Phe Pro Cys Ala Leu Ile Asn Lys
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Tyr Leu Lys Cys Gln Gln Leu Leu
1               5

<210> SEQ ID NO 91
<211> LENGTH: 30
<212> TYPE: PRT

```
<213> ORGANISM: Homo sapiens

<400> SEQUENCE: 91

Thr Glu Asp Pro Gly Pro Asp Glu Ala Pro Arg Met Pro Glu Ala Ala
1               5                   10                  15

Pro Pro Val Ala Pro Ala Pro Ala Ala Pro Thr Pro Ala Ala
            20                  25                  30

<210> SEQ ID NO 92
<211> LENGTH: 30
<212> TYPE: PRT
<213> ORGANISM: Homo sapiens

<400> SEQUENCE: 92

His Ser Gly Thr Ala Lys Ser Val Thr Cys Thr Tyr Ser Pro Ala Leu
1               5                   10                  15

Asn Lys Met Phe Cys Gln Leu Ala Lys Thr Cys Pro Val Gln
            20                  25                  30

<210> SEQ ID NO 93
<211> LENGTH: 30
<212> TYPE: PRT
<213> ORGANISM: Homo sapiens

<400> SEQUENCE: 93

Leu Glu Asp Ser Ser Gly Asn Leu Leu Gly Arg Asn Ser Phe Glu Val
1               5                   10                  15

Arg Val Cys Ala Cys Pro Gly Arg Asp Arg Arg Thr Glu Glu
            20                  25                  30
```

P53 PEPTIDE VACCINE

RELATED APPLICATIONS

This is a continuation of International patent application number PCT/NL2008/050319, filed on May 27, 2008, which claims priority to European patent application no. 07109287.8, filed on May 31, 2007; U.S. Provisional patent application No. 60/941,070, filed on May 31, 2007 European patent application no. 07109802.4, filed on Jun. 7, 2007; and U.S. Provisional patent application No. 60/942,483, filed on Jun. 7, 2007, the entirety of which are herein incorporated by reference.

SEQUENCE LISTING

The instant application contains a Sequence Listing which has been submitted via EFS-Web and is hereby incorporated by reference in its entirety. Said ASCII copy, created on Feb. 19, 2010, is named 85119306.txt, and is 33,841 bytes in size.

FIELD OF THE INVENTION

The present invention relates to the field of medicine and immunology. In particular it relates to an improved p53 peptide vaccine.

BACKGROUND OF THE INVENTION

In this application p53, is taken as a representative example of an ubiquitously expressed self-antigen known to be associated with cancer. The strategy used to design a vaccine against p53 could be applied to design a vaccine against any other ubiquitously expressed self-antigen known to be associated with cancer.

The nuclear phosphoprotein p53 is a tumor suppressor protein that is ubiquitously expressed at low levels in normal tissues, including thymus, spleen and lymphohematopoetic cells (Rogerl A et al, Milner J et al, Terada N et al). The normal half-life of wild-type p53 is less than 30 minutes. Following ubiquitination, the wild-type (WT) p53 protein is rapidly degraded by proteasomes (Honda R et al, Momand J et al, Shkedy D et al). Proteasome-mediated digestion of p53 may lead to the generation of peptides that are presented by class I MHC molecules. Recognition of these class I MHC bound wild-type p53 derived peptides at the surface of thymic APC by immature thymic T-cells with high avidity for the class I MHC-peptide complex will result in negative selection (Allen P M et al, Ashton-Rickardt P G et al, Kappler J W et al). As a consequence, the peripheral T-cell repertoire will not contain functional p53-specific class I MHC-restricted T-cells. Theobald et al. elegantly showed that CTL specific for the naturally processed peptide $p53_{187\text{-}197}$ were deleted from the repertoire in WTp53 mice but not in p53−/− mice (Theobald M et al, 1997), demonstrating that negative selection of high avidity p53-specific CTL can occur in the thymus. Paradoxically, class I MHC-restricted CTL able to recognize endogenously processed WTp53 at the surface of tumor cells, have been detected in both mice and man (Theobald M et al 1997, Macagno A, et al, Mayordomo J I et al, Barfoed A M et al, Chikamatsu K et al, Eura M et al, Houbiers J G et al, Ropke M et al) suggesting that functional p53-specific class I MHC-restricted CTL can escape from tolerance induction.

Several p53 vaccines have already been developed. For example, WO 00/75336 discloses polyepitopic peptides derived from p53 having the capacity to be degraded by the proteasome and to associate with high affinity to class I MHC molecules. Such properties are supposed to be essential for inducing an immune response against p53. More likely, T-cells responding to this type of peptides have either been deleted in the thymus, are tolerized in the periphery or are of low T-cell receptor affinity to mediate an effective anti-tumor response (Theobald M & Offring a R. 2003, and Morgan et al.) Thus, it is to be expected that such peptides derived from an ubiquitously expressed self-antigen, such as p53, will not be able to trigger a strong and effective immune response in vivo.

Therefore, there is still a need for new and improved p53 vaccines, which does not have all the drawbacks of existing p53 vaccines.

DESCRIPTION OF THE INVENTION

The present invention is based on the surprising finding that in order to induce an efficient anti p53 response, a peptide derived from p53 should be inefficiently processed by the proteasome and/or exhibit low to intermediate capacity to stably form cell surface class I MHC-peptide complexes and/or a peptide exhibits a low to intermediate MHC binding affinity. Preferably, a peptide derived from p53 should be inefficiently processed by the proteasome and/or exhibit low to intermediate capacity to stably form cell surface class I MHC-peptide complexes.

We have found that escape of self-specific T-cells from negative selection in the thymus may occur through low-avidity interactions between the TCR and MHC. Indeed, WTp53-specific CTL that recognizes their cognate peptide have been detected in WTp53-mice but with a 10-fold lower avidity than CTL obtained from p53−/− mice (Theobald M et al, 1997 and Hernandez J et al). Furthermore, a disparity between so-called household proteasomes and immunoproteasomes in the generation of certain peptide epitopes may allow positive selection by thymic epithelium but failure to delete these cells by a lack of presentation of these MHC-peptide complexes by thymic APC. Dendritic cells constitutively express immunoproteasomes (Kloetzel P M & Ossendorp 2004) and high levels of immunoproteasomes have been detected in the thymus (Zanelli E et al, and Stohwasser R et al). Morel et al. demonstrated that human CTL recognizing the melanoma antigen Melan-A as well as CTL that recognized a novel ubiquitously expressed protein did not recognize APC carrying immunoproteasomes whereas they were capable of recognizing cells expressing household proteasomes. Failure to present enough class I MHC-molecules presenting the same peptide may also allow T-cells to survive thymic selection (Sebzda E et al). A modest surface expression of certain class I MHC-restricted peptides can be achieved by several, not mutually exclusive, mechanisms: 1) to low expression or to low turn-over of proteins in the cell resulting in the generation of insufficient numbers of epitopes that allow recognition by CTL (Vierboom M P et al), 2) peptides with only a weak binding affinity for MHC may lose the competition with peptides with better MHC-binding properties and as such are scarcely expressed at the cell surface, 3) peptides with only a weak capacity to stably bind to class I MHC may form class I MHC-peptide complexes at the cell surface which quickly disintegrate and as such are not stimulatory to T-cells anymore (van der Burg S H et al 1996) and 4) proteosomal generation of CTL epitopes may be insufficient to generate effective numbers of MHC-peptide complexes.

Peptide

Therefore, in a first aspect, there is provided a peptide derived from a protein that is ubiquitously expressed self-antigen and known to be associated with cancer, said peptide comprising an epitope exhibiting a low to intermediate capacity to form stable class I MHC-peptide complexes at the cell surface and/or being inefficiently processed by a proteasome and/or exhibiting a low to intermediate MHC binding affinity. Preferably, a peptide comprises an epitope exhibiting a low to intermediate capacity to form stable class I MHC-peptide complexes at the cell surface and/or being inefficiently processed by a proteasome.

In the context of the invention, "exhibiting a low to intermediate MHC binding affinity" preferably means that the relative binding affinity of an epitope contained in a peptide is comprised between 5 and 50 μM. More preferably, the relative binding affinity is comprised between 10 and 50 μM, even more preferably between 15 and 50 μM. The relative binding affinity is preferably assessed by a competition based cellular binding assay as previously described (van der Burg S H 1995) (see also example 1). The affinity of a given epitope present within a peptide is expressed as the epitope concentration to inhibit 50% (IC50) of the binding of a reference epitope. The length of the epitope is generally comprised between 8 and 12 amino acids in length and is typically selected based on typical anchor residues for HLA-A*0101, A*0301, A*1101 and A*2401 (Rammensee H G et al). Preferred peptides are the ones as described in example 1.

In the context of the invention, "exhibiting a low to intermediate MHC binding affinity" is preferably measured by measuring the stability for binding to MHC as described in (van der Burg S H et al 1996).

Stability of other peptide-HLA complexes was preferably determined as follows. Peptide binding was performed at 4° C. and 20° C. and $IC_{50}$ were determined. Peptides of >50% of the initial complexes was lost within 2 hours were considered unstable. Stable peptides displayed $IC_{50}$ at 20° C. that deviated <2 times of the $IC_{50}$ at 4° C. Peptides that displayed $IC_{50}$ at 20° C. of more than twice the $IC_{50}$ at 4° C. but $IC_{50}$<15 μM were considered to bind with intermediate stability. The rest was designated as unstable peptide binding.

In the context of the invention, "being inefficiently processed by a proteasome" preferably means that within the first hour of digestion by a proteasome less than 1% of total digested peptide is found. The processing by a proteasome is preferably assessed by incubating a purified proteasome, more preferably a human proteasome with a peptide comprising the potential CTL epitope (30 amino acid length approximately) in a proteasome digestion buffer during at least one hour at 37° C. The reaction is subsequently stopped by adding trifluoroacetic acid. Analysis of the digested peptides is performed with electrospray ionization mass spectrometry (see example 1). Even more preferably, the human proteasome is an immunoproteasome from B-LCL JY cells (Kessler J H et al. 2001).

The sequence of a peptide used in the present invention is not critical as long as it is derived from a protein ubiquitously expressed self-antigen and known to be associated with cancer and as long as the peptide comprises an epitope exhibiting a low capacity to form stable class I MHC at the cell surface and/or which is inefficiently processed by a proteasome and/or exhibiting a low to intermediate MHC binding affinity. Preferably, a peptide comprises an epitope exhibiting a low capacity to form stable class I MHC at the cell surface and/or which is inefficiently processed by a proteasome Accordingly, a peptide is preferably used, which comprises a contiguous amino acid sequence derived from the amino acid sequence of a protein ubiquitously expressed self-antigen and know to be associated with cancer.

In the context of the invention, a protein is ubiquitously expressed. Preferably, a protein is ubiquitously expressed when it is broadly expressed. Broadly preferably means that its expression is detectable by means of arrays or Northern in at least 5 distinct types of tissues including the thymus, more preferably at least 7, including the thymus and even more preferably at least 10, including the thymus.

A protein is preferably said to be associated with cancer in the following illustrating and non-limitative cases: a protein is over-expressed and/or is mutated and/or is aberrantly expressed in a given tissue of cancer patients by comparison with the corresponding tissue of a subject not having cancer. An aberrantly expressed protein may be de novo expressed in a tissue wherein it is normally not expressed. A mutated protein may be a splice variant. A mutated protein may further be produced as an aberrant fusion protein as a result of a translocation.

Examples of proteins that are ubiquitously expressed self-antigens known to be associated with cancer are p53, MDM-2, HDM2 and other proteins playing a role in p53 pathway, molecules such as survivin, telomerase, cytochrome P450 isoform 1B1, Her-2/neu, and CD19 and all so-called house hold proteins.

In a preferred embodiment, the protein is p53, more preferably human p53. The amino acid sequence of human p53 is depicted in SEQ ID No.1 Preferably, the length of the contiguous amino acid sequence derived from the protein, preferably p53 is no more than 45 amino acids and comprises at least 19 contiguous amino acids derived from the amino acid sequence of a protein, preferably p53. The length of the contiguous amino acid sequence derived from a protein, preferably p53 comprised within the peptide, preferably is comprised between 19-45, 22-45, 22-40, 22-35, 24-43, 26-41, 28-39, 30-40, 30-37, 30-35, 32-35 33-35, 31-34 amino acids. In another preferred embodiment, a peptide comprises 22, 23, 24, 25, 26, 27, 28, 29, 30, 31, 32, 33, 34, 35, 36, 37, 38, 39, 40, 41, 42, 43, 44, or 45 or more than 45 contiguous amino acid residues of a protein, preferably p53. The skilled person will therefore understand that a peptide of the invention is distinct from a p53 protein, preferably from the human p53. In another preferred embodiment, a peptide of the invention consists of any of the contiguous amino acid sequences from a protein, preferably p53 as defined herein. A peptide of such length used in the invention may be easily synthesized.

In a preferred embodiment, an antigen present in a peptide derives from a protein, preferably p53 or an immunogenic part, derivative and/or analogue thereof. This peptide should meet the activities as earlier defined herein (a peptide comprises an epitope displaying a low to intermediate capacity to form stable cell-surface expressed class I MHC-peptide complexes and/or being inefficiently processed by a proteasome and/or exhibiting a low to intermediate MHC binding affinity. Preferably, a peptide comprises an epitope displaying a low to intermediate capacity to form stable cell-surface expressed class I MHC-peptide complexes and/or being inefficiently processed by a proteasome). An immunogenic part, derivative and/or analogue of a protein, preferably p53 comprises the same immunogenic capacity in kind not necessarily in amount as said protein itself. A derivative of such a protein can be obtained by preferably conservative amino acid substitution.

In a preferred embodiment, when the protein is p53, several epitopes displaying a low to intermediate capacity to form stable cell-surface expressed class I MHC-peptide complexes have already been identified and are presented in table 5. In this preferred embodiment, a peptide of the invention comprises any of these HLA A1, A2, A3, A11 and/or A24 type epitopes:

A1: 229-236 and/or
A2 149-157 and/or
A3: 101-110, 112-120, 113-120, 117-126, 154-163, 156-163, 360-370, 363-372, 373-381, 376-386 and/or
A11: 101-110, 112-120, 283-291, 311-319, 311-320, 312-319, 363-370-374-382 and/or
A24: 340-348.

Alternatively or in combination with the previous preferred embodiment, in another preferred embodiment, when the protein is p53, epitopes which are inefficiently processed by a proteasome have already been identified and are presented in table 5. In this preferred embodiment, a peptide of the invention comprises any of these HLA A1, A2, A3 and/or A11 type epitopes:

A1: 117-126, 196-205, 229-236 and/or
A2: 264-272 and/or
A3: 101-110, 154-163, 154-164, 156-163, 156-164, 172-181, 376-386 and/or
A11: 101-110, 156-164, 311-319, 311-320, 312-319, 374-382.

Alternatively or in combination with one or two of the previous preferred embodiments, in a preferred embodiment, when the protein is p53, several epitopes exhibiting a low to intermediate MHC binding affinity have already been identified and are presented in table 5. In this preferred embodiment, a peptide of the invention comprises any of these HLA A1, A2, A3, and/or A11 type epitopes:

A1: 117-126, 196-205, 205-214, 229-236, 229-236, and/or
A2: 113-122, 149-157, 264-272, 322-330, and/or
A3: 112-120, 113-120, 117-126, 154-163, 156-163, 172-181, 360-370, 363-372, 373-381 and/or
A11: 112-120, 283-291, 363-370, 374-382.

In an even more preferred embodiment, first two preferred embodiments are combined to define several epitopes, when the protein is p53, said epitopes displaying a low to intermediate capacity to form stable cell-surface expressed class I MHC-peptide and being inefficiently processed by a proteasome. In this even more preferred embodiment, a peptide of the invention comprises any of these HLA A1, A3, and/or A11 type epitopes:

A1: 229-236 and/or
A3: 101-110, 154-163, 156-163, 376-386 and/or
A11: 101-110, 311-319, 311-320, 312-319, 374-382.

Within this even more preferred embodiment, epitopes A1: 229-236, A3: 154-163, 156-163 and/or A11: 374-382 are most preferred since each of these also exhibits a low to intermediate MHC binding affinity.

In one embodiment, a p53 peptide does not consist of or comprise an HLA-A2.1 type epitope. In this embodiment, preferably a p53 peptide does not consist of or comprise an epitope exhibiting a low to intermediate MHC binding affinity.

In a more preferred embodiment, when the protein is p53, the peptide is selected from the following peptides, each peptide comprises or consists of or overlaps with any of the following sequences:
p53 86-115, p53 102-131, p53 142-171, p53 157-186, p53 190-219, p53 224-248, p53 225-254, p53 257-286, p53 273-302, p53 305-334, p53 353-382 and p53 369-393.

Even more preferably, when the protein is p53, the peptide is selected from the following peptides, each peptide comprises or consists of or overlaps with any of the following sequences: p53 142-171, p53 157-186, p53 190-219, p53 224-248, p53 225-254, p53 241-270, p53 257-286 and p53 273-302.

In the context of the invention, overlapping means that the sequence of the peptide partially or completely overlaps with a given sequence. Preferably, overlapping means partially overlapping. Partially preferably means that the overlap is of one or more amino acids at the N-terminus and/or at the C-terminus of the peptide sequence, more preferably of two or more amino acids at the N-terminus and/or at the C-terminus, or more. It is also preferred that the overlap is of one or more amino acids at the N-terminus and/or two or more amino acids at the C-terminus of the peptide sequence or vice versa. The skilled person will understand that all kinds of overlaps are encompassed by the present invention as long as the obtained peptide exhibits the desired activity as earlier defined herein.

Even more preferably, the peptide does not consist of p53 102-137, p53 106-137, p53 149-169, p53 129-156, p53 187-212, p53 187-220, p53 187-205, p53 187-234, p53 226-243 or p53 226-264. Each of these p53 peptides is known from the prior art to exhibit a high MHC binding affinity and/or is efficiently processed by a proteasome Composition In a second aspect of the invention, there is provided a composition comprising one or more of the peptides as defined herein above. Preferably the composition comprises at least two or at least three or at least four, or at least five, or at least six or more of such peptides.

Preferred compositions include at least two of, or at least three of or the following peptides: p53 142-171, p53 157-186, p53 190-219, p53 224-248, p53 225-254, p53 241-270, p53 257-286 and p53 273-302, p53 305-334, p53 353-382 and p53 369-393. More preferred compositions further include p53 86-115 and/or p53 102-131.

In yet other preferred embodiments, the composition comprises at least one of the following pools of peptides, wherein each peptide comprises or consists of or overlaps with the following sequences:
pool 1: p53 190-219, p53 206-235, p53 224-248,
pool 2: p53 142-171, p53 157-186, 174-203,
pool 3: p53 225-254, p53 241-270, p53 257-286, p53 273-302, p53 289-318, p53 305-334, p53 321-350, p53 337-366, p53 353-382 and p53 369-393,
pool 4: p53 102-131, p53 126-155,
pool 5: p53 70-99[[0]], p53 86-115.

The art currently knows many ways of generating a peptide. The invention is not limited to any form of generated peptide as long as the generated peptide comprises, consists or overlaps with any of the given sequences and had the required activity as earlier defined herein. By way of example, a peptide present in the composition may be obtained from a protein, preferably p53 synthesized in vitro or by a cell, for instance through an encoding nucleic acid. A peptide may be present as a single peptide or incorporated into a fusion protein. A peptide may further be modified by deletion or substitution of one or more amino acids, by extension at the N- and/or C-terminus with additional amino acids or functional groups, which may improve bio-availability, targeting to T-cells, or comprise or release immune modulating substances that provide adjuvant or (co)stimulatory functions. The optional additional amino acids at the N- and/or C-terminus are preferably not present in the corresponding positions in the amino acid sequence of the protein it derives from, preferably p53 amino acid sequence.

Accordingly, in a further aspect a peptide of the invention and a composition of the invention as herein defined are for use as a medicament.

In a further preferred embodiment, a peptide or a peptide composition further comprises a pharmaceutical excipient and/or an immune modulator. Any known inert pharmaceutically acceptable carrier and/or excipient may be added to the composition. Formulation of medicaments, and the use of pharmaceutically acceptable excipients are known and customary in the art and for instance described in Remington; The Science and Practice of Pharmacy, 21$^{nd}$ Edition 2005, University of Sciences in Philadelphia. A peptides of the invention is preferably soluble in physiologically acceptable watery solutions (e.g. PBS) comprising no more than 35 decreasing to 0%; 35, 20, 10, 5 or 0% DMSO. In such a solution, a peptide is preferably soluble at a concentration of at least 0.5, 1, 2, 4, or 8 mg peptide per ml. More preferably, a mixture of more than one different peptides of the invention is soluble at a concentration of at least 0.5, 1, 2, 4, or 8 mg peptide per ml in such solutions.

Any known immune modulator, may be added to the composition. Preferably, the immune modulator is an adjuvant. More preferably, the composition comprises a peptide as earlier defined herein and at least one adjuvant. Preferably, the adjuvant is an oil-in-water emulsion such as incomplete Freunds Adjuvants, MONTANIDE™ ISA51 (Seppic, France), MONTANIDE™ 720 (Seppic, France). This type of medicament may be administered as a single administration. Alternatively, the administration of a peptide as earlier herein defined and/or an adjuvant may be repeated if needed and/or distinct peptides and/or distinct adjuvants may be sequentially administered.

Particularly preferred adjuvants are those that are known to act via the Toll-like receptors. Adjuvants that are capable of activation of the innate immune system, can be activated particularly well via Toll like receptors (TLR's), including TLR's 1-10 and/or via a RIG-1 (Retinoic acid-inducible gene-1) protein and/or via an endothelin receptor. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heatshock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines and derivatives. TLR9 may be activated by unmethylated CpG DNA or chromatin—IgG complexes. In particular TLR3, TLR4, TLR7 and TLR9 play an important role in mediating an innate immune response against viral infections, and compounds capable of activating these receptors are particularly preferred for use in the invention. Particularly preferred adjuvants comprise, but are not limited to, synthetically produced compounds comprising dsRNA, poly(I:C), unmethylated CpG DNA which trigger TLR3 and TLR9 receptors, IC31, a TLR9 agonist, IMSAVAC, a TLR4 agonist. In another preferred embodiment, the adjuvants are physically linked to a peptide as earlied defined herein. Physical linkage of adjuvants and costimulatory compounds or functional groups, to the HLA class I and HLA class II epitope comprising peptides provides an enhanced immune response by simultaneous stimulation of antigen presenting cells, in particular dendritic cells, that internalize, metabolize and display antigen. Another preferred immune modifying compound is a T cell adhesion inhibitor, more preferably an inhibitor of an endothelin receptor such as BQ-788 (Buckanovich R J et al, Ishikawa K, PNAS (1994) 91:4892). BQ-788 is N-cis-2,6-dimethylpiperidinocarbonyl-L-gamma-methylleucyl-D-1-methoxycarbonyltryptophanyl-D-norleucine. However any derivative of BQ-788 or modified BQ-788 compound is also encompassed within the scope of this invention.

Furthermore, the use of APC (co)stimulatory molecules, as set out in WO99/61065 and in WO03/084999, in combination with a peptide present in the medicament used in the invention is preferred. In particular the use of 4-1-BB and/or CD40 ligands, agonistic antibodies or functional fragments and derivates thereof, as well as synthetic compounds with similar agonistic activity are preferably administered separately or combined with a peptide present in the medicament to subjects to be treated in order to further stimulate the mounting an optimal immune response in the subject.

In a preferred embodiment, the adjuvant comprises an exosome, a dendritic cell, monophosphoryl lipid A and/or CpG nucleic acid.

Therefore in a preferred embodiment, a medicament comprises a peptide or a composition as earlier defined herein and an adjuvant selected from the group consisting of: oil-in water emulsions (MONTANIDE™ ISA51, MONTANIDE™ ISA 720), an adjuvant known to act via a Toll-like receptor, an APC-costimulatory molecule, an exosome, a dendritic cell, monophosphoryl lipid A and a CpG nucleic acid.

In another preferred embodiment, to promote the presentation of a peptide by a professional antigen presenting cell or dendritic cells, the medicament comprising a peptide further comprises a DC-activating agent.

Ways of administration are known and customary in the art are for instance described in Remington; The Science and Practice of Pharmacy, 20 Edition 2005, University of Sciences in Philadelphia. Peptide, peptide compositions and pharmaceutical compositions and medicaments of the invention are preferably formulated to be suitable for intravenous or subcutaneous, or intramuscular administration, although other administration routes can be envisaged, such as mucosal administration or intradermal and/or intracutaneous administration, e.g. by injection. Intradermal administration is preferred herein. Advantages and/or preferred embodiments that are specifically associated with intradermal administration are later on defined in a separate section entitled "intradermal administration".

It is furthermore encompassed by the present invention that the administration of at least one peptide and/or at least one composition of the invention may be carried out as a single administration. Alternatively, the administration of at least one peptide and/or at least one composition may be repeated if needed and/or distinct peptides and/or compositions of the invention may be sequentially administered.

Any way of administration of the composition or medicament of the invention may be used. The composition or medicament of the invention may be formulated to be suitable for intravenous or subcutaneous, or intramuscular administration, although other administration routes may be envisaged, such as mucosal or intradermal and/or intracutaneous administrations, e.g. by injection.

In addition a preferred embodiment comprises delivery of a peptide, with or without additional immune stimulants such as TLR ligands and/or anti CD40/anti-4-1 BB antibodies in a slow release vehicle such as mineral oil (e.g. MONTANIDE™ ISA 51) or PLGA. Alternatively, a peptide of the invention may be delivered by intradermally, e.g. by injection, with or without immune stimulants (adjuvants). Preferably for intradermal delivery a peptide of the invention is administered in a composition consisting of the peptides and one or more immunologically inert pharmaceutically acceptable carriers, e.g. buffered aqueous solutions at physiological ionic strength and/or osmolarity (such as e.g. PBS).

Use of a Peptide

In a further aspect of the invention, there is provided a use of a peptide as earlier defined herein derived from a ubiquitously expressed self-antigen known to be associated with cancer, said peptide exhibiting a low to intermediate capacity to form stable cell surface expressed class I-MHC complexes and/or being inefficiently processed by a proteasome and/or exhibiting a low to intermediate MHC binding affinity for the manufacture of a medicament for the treatment or prevention of cancer. Preferably, the protein is p53. Preferably, a peptide exhibits a low to intermediate capacity to form stable cell surface expressed class I-MHC complexes and/or is inefficiently processed by a proteasome.

Preferred peptides for use in the treatment or prevention of cancer are as already defined herein above.

All preferred features of the medicament manufactured for this use have already been defined earlier herein. In a preferred embodiment, the medicament which is used further comprises an inert pharmaceutically acceptable carrier and/or an adjuvant. In a preferred embodiment, the medicament, which is a vaccine, is administered to a human or animal. In a more preferred embodiment, the human or animal is suffering from or at risk of suffering from a cancer, wherein the protein the peptide derives from is associated with. More preferably, the protein is p53, even more preferably human p53. Even more preferably, cancer associated with p53 are selected among the following list: lung, colon, esophagus, ovary, pancreas, skin, gastric, head and neck, bladder, sarcoma, prostate, hepatocellular, brain, adenal, breast, endometrium, mesothelioma, renal, thyroid, hematologic, carcinoid, melanoma, parathyroid, cervix, neuroblastoma, Wilms, testes, pituitary and pheochromocytoma cancers.

Other preferred proteins have been already cited herein.

Preferably, said disease such as cancer is at least in part treatable or preventable by inducing and/or enhancing said immune response using a peptide of the invention.

A method of the invention is therefore very suited for providing a subject with immunity against any ubiquitously expressed self protein known to be associated with cancer and/or for enhancing said immunity. Methods of the invention are suitable for any purpose that other immunization strategies are used for. Of old immunizations are used for vaccination purposes, i.e. for the prevention of cancer. However, methods of the invention are not only suitable for preventing cancer. Methods can also be used to treat existing cancer, of course with the limitations that the cancer is treatable by inducing and/or enhancing antigen specific T cell immunity.

Method

In a further aspect, the invention provides a method for designing a peptide derived from a protein ubiquitously expressed self-antigen associated with cancer, said peptide comprising an epitope exhibiting a low to intermediate capacity to form stable cell surface expressed class I-MHC complexes and/or being inefficiently processed by a proteasome and/or exhibiting a low to intermediate MHC binding affinity and said peptide being suitable for the manufacture of a medicament for the treatment or prevention of cancer. Preferred peptide comprises an epitope exhibiting a low to intermediate capacity to form stable cell surface expressed class I-MHC complexes and/or being inefficiently processed by a proteasome.

All features of this method have already been explained herein.

To identify such a peptide the skilled person could follow the strategy as illustrated in the examples: an epitope exhibiting a low to intermediate MHC binding affinity may be identified by measuring the relative binding affinity as earlier defined herein. The capacity of an epitope to form a low/intermediate stable cell surface expressed class I-MHC complexes may be measured as earlier defined herein. Finally, the inefficiently processing of a peptide by a proteasome may be assessed as earlier defined herein.

Intradermal Administration

In a preferred embodiment, a peptide or a composition comprising a peptide or a medicament used in the invention all as defined herein are formulated to be suitable for intradermal administration or application. Intradermal is known to the skilled person. In the context of the invention, intradermal is synonymous with intracutaneous and is distinct from subcutaneous. A most superficial application of a substance is epicutaenous (on the skin), then would come an intradermal application (in or into the skin), then a subcutaneous application (in the tissues just under the skin), then an intramuscular application (into the body of the muscle). An intradermal application is usually given by injection. An intradermal injection of a substance is usually done to test a possible reaction, allergy and/or cellular immunity to it. A subcutaneous application is usually also given by injection: a needle is injected in the tissues under the skin.

In another further preferred embodiment, a medicament or composition or peptide used in the invention does not comprise any adjuvant such as MONTANIDE™ ISA-51, it means the formulation of the medicament (or composition or peptide) is more simple: an oil-water based emulsion is preferably not present in a medicament (or composition or peptide) used. Accordingly, a medicament (or composition or peptide) used in the invention does not comprise an adjuvant such as MONTANIDE™ ISA-51 and/or does not comprise an oil-in-water based emulsion. Therefore, in a preferred embodiment, a medicament (or composition or peptide) used in the invention is a buffered aqueous solutions at physiological ionic strength and/or osmolarity, such as e.g. PBS (Phosphate Buffer Saline) comprising or consisting of one or more peptide as defined earlier herein. The skilled person knows how to prepare such a solution.

A medicament (or composition or peptide) as used in the invention has another advantage, which is that by intradermally administering low amounts of a peptide as earlier herein defined, an immunogenic effect may still be achieved. The amount of each peptide used is preferably ranged between 1 and 1000 μs, more preferably between 5 and 500 μg, even more preferably between 10 and 100 μg.

In another preferred embodiment, a medicament (or composition) comprises a peptide as earlier defined herein and at least one adjuvant, said adjuvant being not formulated in an oil-in water based emulsion and/or not being of an oil-in-water emulsion type as earlier defined herein. This type of medicament may be administered as a single administration. Alternatively, the administration of a peptide as earlier herein defined and/or an adjuvant may be repeated if needed and/or distinct peptides and/or distinct adjuvants may be sequentially administered. It is further encompassed by the present invention that a peptide of the invention is administered intradermally whereas an adjuvant as defined herein is sequentially administered. An adjuvant may be intradermally administered. However any other way of administration may be used for an adjuvant.

The intradermal administration of a peptide is very attractive since the injection of the vaccine is realized at or as close by as possible to the site of the disease resulting in the local activation of the disease draining lymph node, resulting in a stronger local activation of the immune system. In a preferred embodiment, the intradermal administration is carried out directly at the site of the lesion or disease. At the site of the lesion is herein understood to be within less than 5, 2, 1, 0.5, 0.2 or 0.1 cm from the site of the lesion.

Upon intradermally administering a medicament as defined herein, not only Th2 but also Th1 responses are triggered. This is surprising since it was already found that cutaneous antigen priming via gene gun lead to a selective Th2 immune response (Alvarez D. et al, 2005). Furthermore, the immune response observed is not only restricted to the skin as could be expected based on (Alvarez D. et al, 2005). We demonstrate that specific T cells secreting IFNγ circulate through the secondary lymph system as they are detected in the post challenged peripheral blood.

Another crucial advantage of a medicament (or composition or peptide) of the invention is that relatively low amounts of a peptide may be used, in one single shot, in a simple formulation and without any adjuvant known to give undesired side-effects as MONTANIDE™ ISA-51. Without wishing to be bound by any theory, we believe that the intradermal peptide(s) used in the invention specifically and directly targets the epidermal Langerhans cells (LC) present in the epithelium. Langerhans cells are a specific subtype of DC which exhibit outstanding capacity to initiate primary immune responses (Romani N. et al 1992). These LC may be seen as natural adjuvants recruited by the medicament used in the invention.

In another preferred embodiment, the invention relates to the use of a peptide as defined herein for the manufacture of a medicament for the treatment or prevention of a disease as defined herein, wherein the medicament is for intradermal administration as earlier defined and wherein in addition a same and/or distinct peptide as defined herein is further used for the manufacture of a medicament for the treatment or prevention of the same disease, wherein the medicament is for subcutaneous administration.

A medicament for intradermal administration has already been defined herein. A peptide used for subcutaneous administration may be the same as the one used for intradermal administration and has already been defined herein. The skilled person knows how to formulate a medicament suited for subcutaneous administration. Preferably, a medicament suited for subcutaneous administration comprises a peptide as already herein defined in combination with an adjuvant. Preferred adjuvants have already been mentioned herein. Other preferred adjuvants are of the type of an oil-in water emulsions such as incomplete Freund's adjuvant or IFA, MONTANIDE™ ISA-51 or MONTANIDE™ ISA 720 (Seppic, France). In a further preferred embodiment, a medicament suited for subcutaneous administration comprises one or more peptides, an adjuvant both as earlier defined herein and an inert pharmaceutically acceptable carrier and/or excipients all as earlier defined herein. Formulation of medicaments, and the use of pharmaceutically acceptable excipients are known and customary in the art and for instance described in Remington; The Science and Practice of Pharmacy, 21$^{nd}$ Edition 2005, University of Sciences in Philadelphia. The second medicament used in the invention is formulated to be suitable for subcutaneous administration.

In this preferred embodiment, a medicament suited for intradermal administration may be simultaneously administered with a medicament suited for subcutaneous administration. Alternatively, both medicaments may be sequentially intradermally and subsequently subcutaneously administered or vice versa (first subcutaneous administration followed by intradermal administration). In this preferred embodiment as in earlier preferred embodiment dedicated to the intradermal administration, the intradermal and/or subcutaneous administration of a peptide as earlier herein defined and/or of an adjuvant may be repeated if needed and/or of distinct peptides and/or of distinct adjuvants may be sequentially intradermally and/or subcutaneously administered. It is further encompassed by the present invention that a peptide of the invention is administered intradermally and/or subcutaneously whereas an adjuvant as defined herein is sequentially administered. The adjuvant may be intradermally and/or subcutaneously administered. However any other way of administration may be used for the adjuvant.

We expect the combination of an intradermal and a subcutaneous administration of a medicament (or a composition or a peptide) according to the invention is advantageous. DC in the epidermis are clearly different from DC in the dermis and in the subcutis. The intracutaneous (intradermal) immunization will cause antigen processing and activation of epidermal DC (Langerin-positive langerhans cells) that through their dendritic network are in close contact with the keratinocytes. This will also optimally activate inflammatory pathways in the interactions between Langerhans cell and keratinocytes, followed by trafficking of antigen loaded and activated Langerhans cell to the skin-draining lymph nodes.

The subcutaneous administration will activate other DC subsets, that will also become loaded with antigen and travel independently to the skin-draining lymph nodes. Conceivably, the use of a medicament which may be administered both intradermally and subcutaneously may lead to a synergistic stimulation of T-cells in these draining nodes by the different DC subsets.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a peptide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way

BRIEF DESCRIPTION OF THE DRAWINGS

FIG. 1. Proteasomal cleavage products. FIG. 1 discloses SEQ ID NOS 91-93, respectively, in order of appearance.

A-F) Vaccine induced response (*) if {mean number of spots−(mean number of spots in medium+2SD)>10 spots} AND post-vaccination value≥2× pre-vaccination value. Light grey bars: pre-vaccination, black bars: post-vaccination.

FIG. 7. P53-peptide specific responses in skin biopsies of vaccination sites obtained from ovarian cancer patients as measured by proliferation assay (n=7). Biopsies are taken three weeks after the last vaccination from the last injection site. A-D) Vaccine induced response (*) if counts per minute ≥1000 and proliferation index ≥3.

Figure 8:
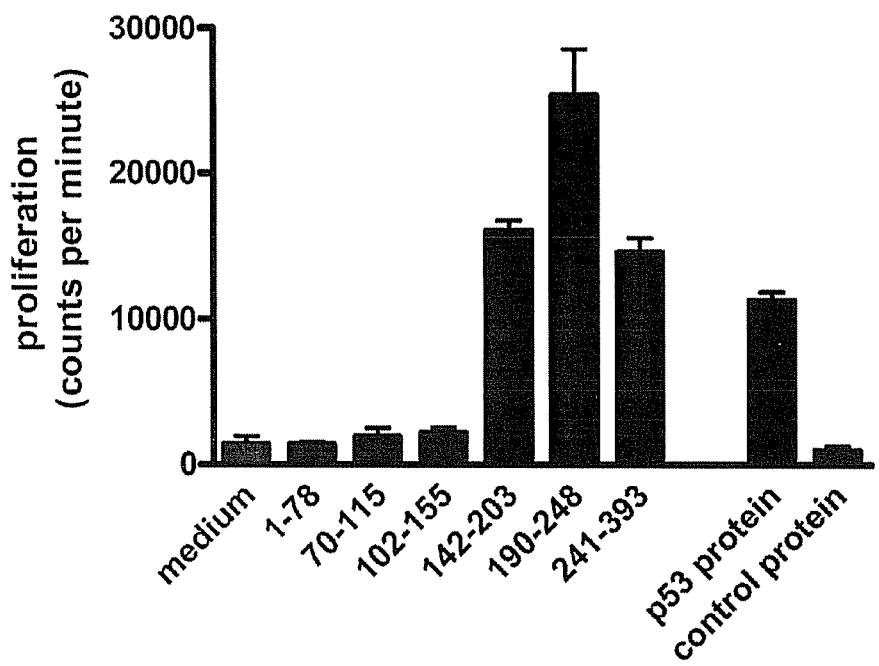

FIG. 8. Vaccine-induced p53-specific T-cells can migrate into areas where p53 antigen is present and recognize naturally processed and presented p53 protein.

A biopsy of the second vaccine site of a patient with colorectal cancer was taken and skin-infiltrating T-cells were expanded. The skin-infiltrating T-cells were tested against several pools of p53 peptides (indicated by the number of the first and last amino acid of the amino acid sequence of the p53 protein that is covered by the pool of peptides used) as well as p53 protein and control protein. The bars indicate the mean and standard deviation of triplicate wells.

Figure 9:
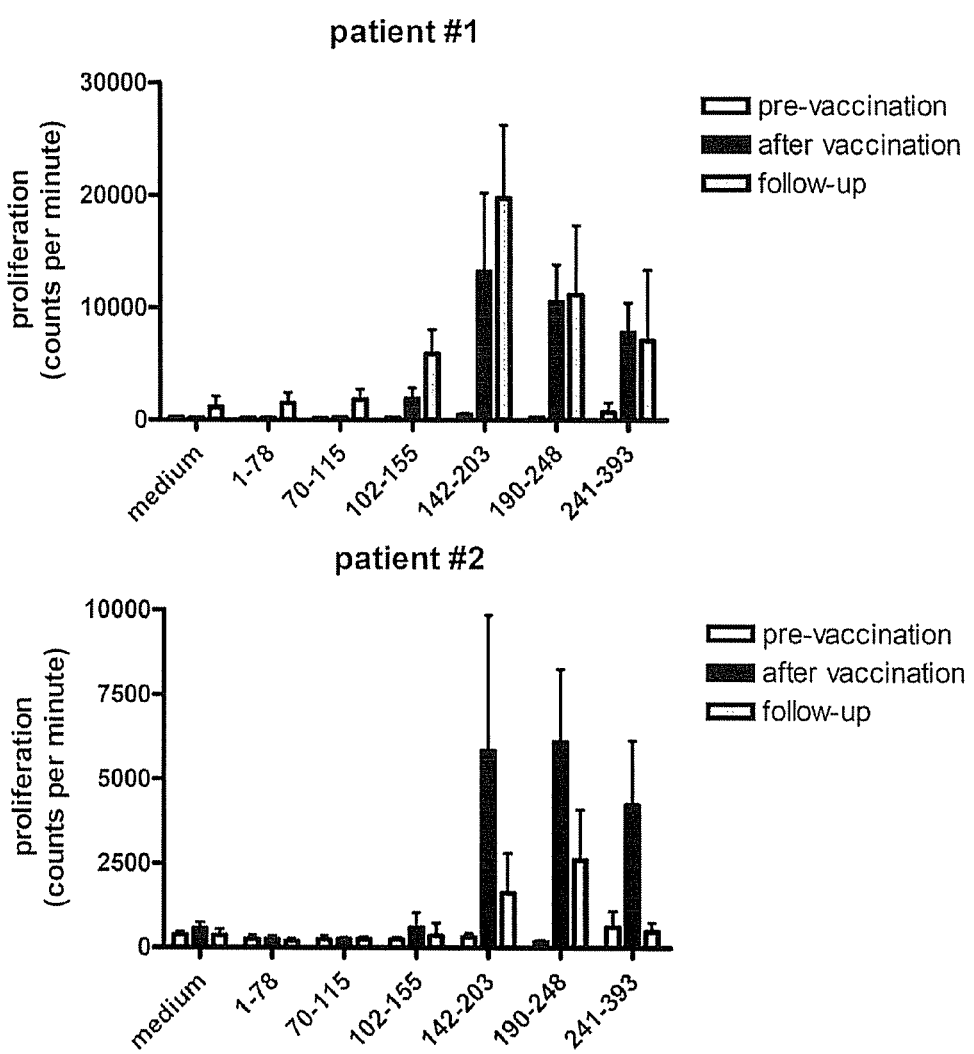

FIG. 9. Vaccination with p53-SLP vaccine induces T-cell memory responses and antigen-spreading in patients with colorectal cancer.

PBMC isolated pre-vaccination, after 2 vaccinations and at 6 months (#1) or 9 months (#2) after vaccination were tested for the presence of p53-specific T-cells in a proliferation assay by stimulating the PBMC for 6 days with several pools of p53 peptides (indicated by the number of the first and last amino acid of the amino acid sequence of the p53 protein that is covered by the pool of peptides used). The bars indicate the mean and standard deviation of 8-wells.

Figure 10:
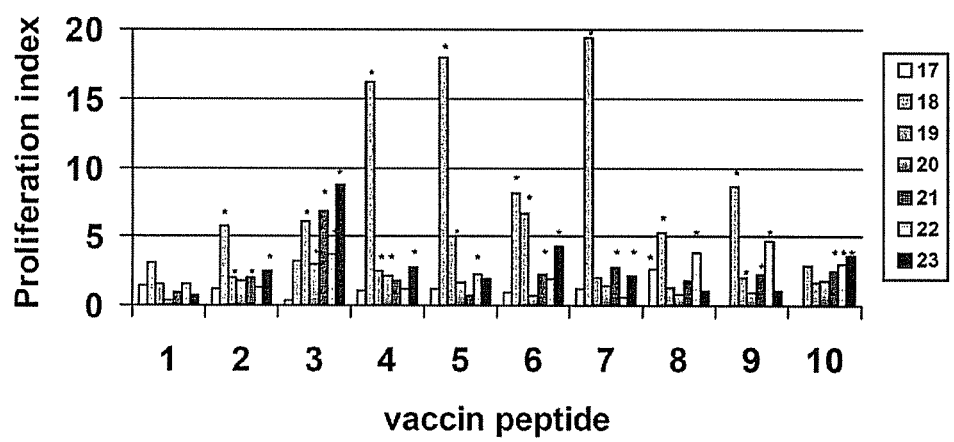

FIG. 10. Responses in ovarian cancer patients to individual p53 synthetic long peptides as measured by proliferation assay after four immunisations. Positive response (*) if ≥1000 cpm & proliferation index ≥2.

FIG. 11. P53-peptide specific responses in skin biopsies of vaccination sites obtained from ovarian cancer patients as measured by proliferation assay.

Biopsies from the last injection site were obtained from 17 ovarian cancer patients three weeks after the last vaccination. Insufficient numbers of lymphocytes for proliferation assay could be cultured from two biopsies (015 & 020). Positive response (*) if counts per minute ≥1000 and proliferation index ≥3.

FIG. 12. P53-specific T-cell responses as measured by proliferation assay before the first and after the last vaccination as well as after subsequent chemotherapy in ovarian cancer patients. Post-chemotherapy samples were obtained 12 months (009) resp. 9 months (019) after the last vaccination and at least one month after the last chemotherapy. Vaccine-induced response (*) if cpm ≥1000 & S.I. ≥3 and if the cpm after vaccination/chemotherapy was ≥2 the pre-vaccination value.

Figure 13A:
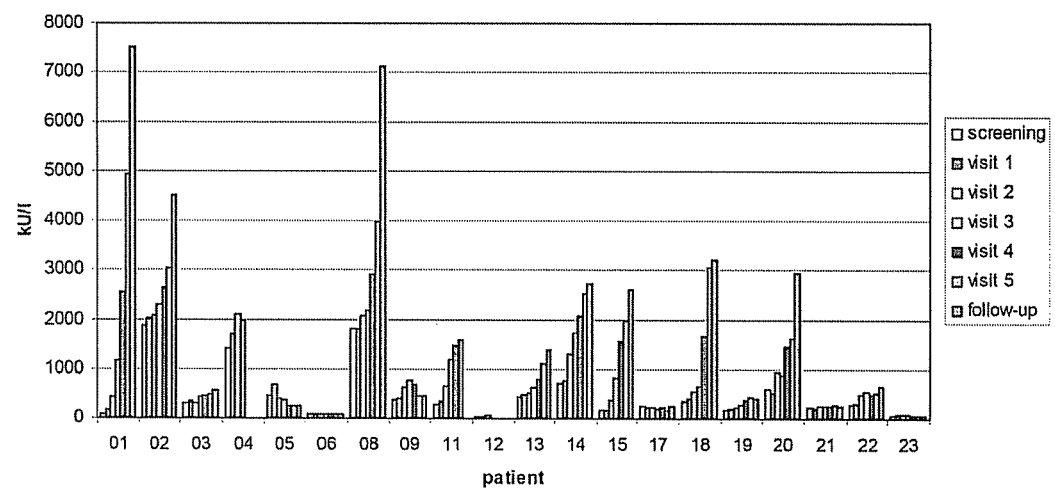
Figure 13B:
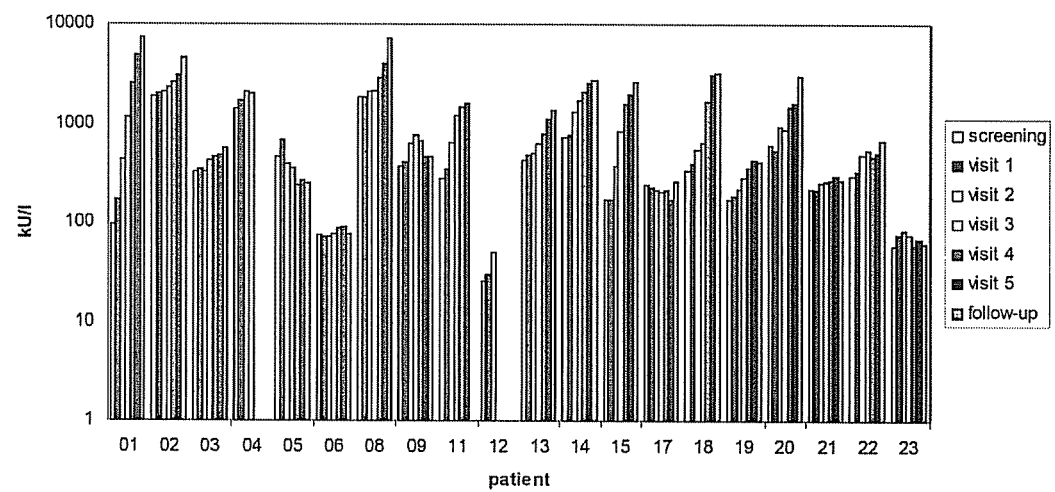

FIG. 13. Serum CA-125 levels in ovarian cancer patients before, during and after vaccination. Missing values: 04 visit 4/5/FU; 05 visit 3/4/5/FU; 11 visit FU FIG. 14: An overview of the number, day of appearance and injected antigen that induced a positive skin reactions in the group of 19 healthy donors (HD). Skin reactions were considered positive when papules greater then 2 mm in diameter arose no less then 2 days after injection. The indicated layout is used for the 8 peptide pools, the first and last amino acid in the protein of the peptide pool used is indicated. The layout printed in bold indicates at least one positive reaction within this timeframe; a filled square represents a new developed, positive skin reaction to the indicated peptide pool.

Figure 15:
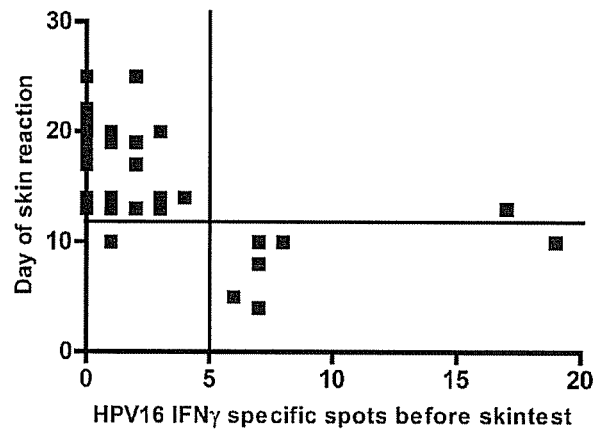

FIG. 15. Detection of HPV16 specific T cells by IFNγ ELIspot in the pre-challenge blood sample of healthy donors is significantly correlated with the appearance of an early (<13 days) positive skin reaction to the recognized peptide pool (p=0.0003, two tailed Fisher's Extract test). Specific responses were calculated by subtracting the mean number of spots+2×SD of the medium control from the mean number of spots in experimental wells. The number of specific spots per 100.000 PBMC is given. Responses were considered positive if peptide pool specific T cell frequencies were ≥5 in 100.000 PBMCs.

Figure 16:
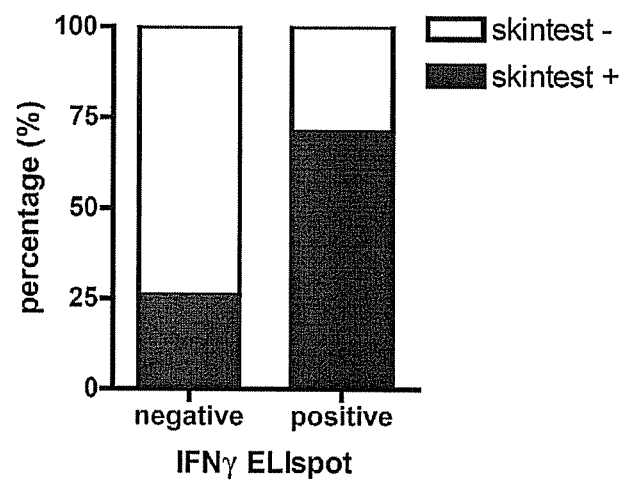

FIG. 16. A. Association between the appearance of a positive skin reaction and the simultaneous detection (IFNγ ELIspot) of circulating HPV 16 specific T cells in the post-challenge blood sample of healthy donors (p<0.0001, two tailed Fisher's exact test). From a total of 88 skin tests, 39 were positive. Twenty-five of these 39 reactions were associated with a positive reaction in ELIspot (T cell frequency ≥5 in 100.000 PBMCs). Of the 49 skin test sites that did not show a skin reaction, 10 were associated with a positive ELIspot.

FIG. 17.

A. HPV16 specific T cell responses detected by IFNγ ELIspot in the post-challenge blood sample of healthy donors displaying a positive skin reaction. The mean number of spots per 100.000 PBMCs are depicted. Memory response mix (MRM) was used as a positive control. The filled bar indicates the positive skin reaction site of which a punch biopsy was taken and put in to culture.

B. T lymphocytes exfiltrating from punch biopsies were, after a 14- to 28 day period of cytokine driven expansion, tested for their capacity to proliferate upon stimulation with monocytes pulsed with peptides (10 μg/ml)—as injected in the skin test- or with protein (20 μg/ml). Phytohemagglutinine (PHA) served as a positive control. Proliferation was measured by [³H]thymidine incorporation and a proliferative response was defined specific as the stimulation index (SI)≥3. Healthy donor 17 (HD17) is an example of a positive skin reaction site consisting of non specific T cells.

C. Supernatants of the proliferative responses in B were analysed for the presence of IFNγ, interleukin 4 (IL4), IL5 and tumor necrosis factor α, IL2, IL10 (not shown) by cytometric bead array. Cutoff values were based on the standard curves of the different cytokines (100 pg/ml IFNγ and 20 pg/ml for the remaining cytokines). Antigen-specific cytokine production was defined as a cytokine concentration above cutoff level and >2× the concentration of the medium control. Healthy donor 15 (HD15) displays a high background level of IL5, but is increased >2× after antigen stimulation.

FIG. 18.

T cell culture of the skin biopsy of pool 4 ($E6_{41-65}$, $E6_{55-80}$, $E6_{71-95}$) of healthy donor 15 (HD15) consists of both HPV16 specific CD4+ and CD8+ T cells. The specificity of the culture was tested in an intracellular cytokine staining (ICS) against the protein (20 μg/ml) and the peptides (10 μg/ml) corresponding with the injected skin test. Remarkably, in 3 out of 4 biopsies CD8+ HPV16-specific T cells were detected.

EXAMPLES

Example 1

Relation Between HLA Binding, Proteasomal Digestion and Tolerance

A modest surface expression of certain class I MHC-restricted peptides can be achieved by several, not mutually exclusive, mechanisms: 1) to low expression or to low turnover of proteins in the cell resulting in the generation of insufficient numbers of epitopes that allow recognition by CTL (Vierboom M P et al), 2) peptides with only a weak binding capacity for MHC may lose the competition with peptides with better MHC-binding properties and as such are scarcely expressed at the cell surface, and 3) proteosomal generation of CTL epitopes may be insufficient to generate effective numbers of MHC-peptide complexes.

As part of normal cell regulation, p53 protein is targeted for proteasome-mediated degradation and shortage of protein entering the proteasome is therefore not likely to play an important role in the escape of negative selection. We have, therefore, analyzed the binding capacity of p53 derived peptides as well as the capacity of immunoproteasomes and household proteasomes to generate these peptides in vitro.

Results and Discussion

From a large set of peptides that were selected based on the presence of so-called major anchor residues for HLA-A*0101, HLA-A*0301, HLA-A*1101 and HLA-A*2401, 43 peptides were found to bind with intermediate to high affinity (Table 1). These peptides and 7 HLA-A*0201 binding peptides (Houbiers J G et al, Nijman H W et al, Theobald M et al 1995) were further in vitro analyzed for both the stability of binding van der Burd S H et al 1995 and 1996) as well as for the liberation of the exact C-terminus by immunoproteasomes and household proteasomes (Kessler J H et al 2001) (Table 1). In general, the results obtained with both types of proteasomes were comparable. Except for the peptides $p53_{110-120}$, $p53_{111-120}$, $p53_{112-120}$, and $p53_{113-120}$ binding to both HLA-A*0301 and/or HLA-A*1101 and carrying the same C-terminal lysine, no disparity in epitope generation between the household and immunoproteasomes was detected (Table 1).

At present, 5 different CTL epitopes in p53 have been identified (Table 2). Four of these epitopes were restricted by HLA-A*0201 and one by HLA-A*2401. Peptide binding analysis revealed that peptide $p53_{264-272}$ displayed intermediate binding affinity and peptide $p53_{149-157}$ displayed a weak capacity to form stable peptide-HLA-A*0201 complexes, the other 4 peptides displayed a good and stable binding to their restricting HLA molecules. Interestingly, proteasomal cleavage analysis of 30 residue long precursor peptides demonstrated that only two ($p53_{149-157}$ and $p53_{187-197}$) out of these five peptides were efficiently generated by both household and immunoproteasomes (FIG. 1). For peptide $p53_{264-272}$ a fragment corresponding to the part after C-terminal cleavage was found after 4 hours of digestion, but the peptide itself or N-terminally extended pre-cursors were not detected (FIG. 1). Recently, it was demonstrated that pre-cursor peptides could be detected after in vitro digestion by 20S proteasomes, albeit at trace amounts (Theobald M et al 1998). Taken together, there are two epitopes $p53_{65-73}$ and $p53_{125-134}$ which display good binding capacity but are not/inefficiently processed by 20S proteasomes whereas a third peptide ($p53_{149-157}$) is well processed by both types of proteasomes but demonstrates a weak capacity to form stable peptide-HLA complexes. Furthermore, $p53_{264-272}$ binds with intermediate affinity to HLA-A*0201 but is not well processed by proteasomes (Table 2). Most likely, the number of MHC-peptide complexes formed by these peptides at the surface of thymic APC is insufficient to delete the corresponding p53-specific CTL, allowing these cells to egress into the periphery. The one peptide ($p53_{187-197}$) that displays good binding capacity to HLA-A*0201, forms stable peptide-HLA complexes and is well generated by both immunoproteasomes and household proteasomes (Table 2) induced T-cell tolerance (Theobald M et al 1997), as was expected. Bearing this in mind, it will be interesting to find out whether the other inefficiently processed peptides, presented in table 1, which bind to either HLA-A*0101, HLA-A*0301, HLA-A*1101 or HLA-A*2401, form genuine CTL epitopes.

We recently reported on the identification of CTL epitopes in the cancer associated self-antigen PRAME (Kessler J H et al 2001). Comparison of the binding capacity and liberation of the C-terminus by proteasomes of p53- and PRAME-derived peptides reveals that the PRAME peptides are well processed whereas the p53-derived CTL epitopes are not (Table 2). PRAME is expressed in a variety of tumors, testis and at low levels in normal endometrium but is not expressed in the thymus and as a result PRAME-specific CTL are not deleted in the thymus. Together these data suggest that the combination of stable peptide binding and proteasomal liberation of exact C-termini may lead to accurate prediction of CTL epitopes for which CTL will be available (e.g. viral antigens, tumor antigens such as PRAME) whereas for ubiquitously expressed antigens such as p53 it may reveal to which peptides tolerance will exist.

Figure 2:
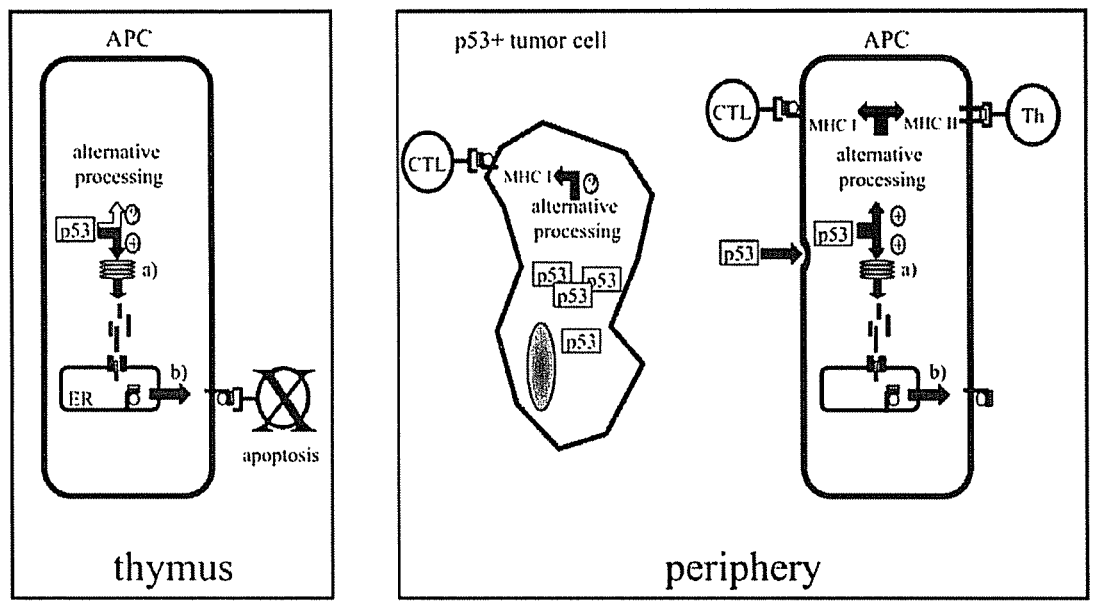
FIG. 2. Explanation of the mechanism of formation of the proteasomal cleavage products.

It has now been well established that CTL epitopes may be generated via alternative processing pathways (Benham A M et al, Glas R et al, Geier E et al, Reimann J et al) and that this results in HLA-class I molecules containing peptides with diverse carboxy termini and from proteins dispersed throughout the cell (Luckey C J et al 1998). A wide variety of tumors display enhanced expression levels of p53, due to mutations in the p53 gene or other genes of the p53 regulatory pathway, as a result of decreased proteasomal digestion (Honda R et al). Interestingly, the expression of the dominant HLA-A*0201-restricted influenza matrix CTL epitope is enhanced when cells are treated with proteasome inhibitors (Luckey C J et al 1998). Furthermore, it was demonstrated that 50-60% of normal expression levels of HLA-A*0201 molecules reappeared at surface despite the presence of proteasome inhibitors (Luckey C J et al 2001). This suggests that proteins that are not/less well degraded by proteasome are more likely to be processed by other ways. This may mean that overexpression of p53 results in an enhanced expression of (amongst others HLA-A*0201-restricted) CTL epitopes generated via other routes than the proteasome (FIG. 2). Activation of p53-specific CTL may occur after uptake of tumor-derived p53 by peripheral APC. This results in the presentation of p53-peptides in the MHC class II pathway (van der Brug S H et al 2001 and Tilkin A F et al) and may also lead to presentation in MHC class I (Reimann J et al) (FIG. 2).

Concluding Remarks

We recently demonstrated that the efficient liberation of the exact C-terminus of putative CTL epitopes present in 25-30 amino acid long precursor peptides by 20S proteasomes, accurately identified natural processed peptides for which CTL are present in the peripheral blood (Kessler J H et al 2001). With respect to ubiquitously expressed antigens that as part of their normal regulation are degraded by the proteasome, some necessary differentiations should be made. A combination of a high capacity to form stable MHC peptide complexes and an efficient liberation by proteasomal digestion renders a peptide to induce tolerance. In contrast, peptides handicapped by either one of these two may form natural targets for CTL that made it to the periphery.

Material and Methods

Peptides, Peptide Binding and Stabilization Assays

Peptides 8-11 residues in length were selected based on typical anchor residues for HLA-A*0101, A*0301, A*1101 and HLA-A*2401 (Rammensee H G et al). The capacity of peptides to bind was tested in a competition based cellular binding assay as previously described (van der Burg S H et al 1995). FL-labeled reference peptides were synthesized as Cys-derivative (van der Burg S H et al 1995). Fluorescence labeled reference peptides used were: YLEPAC(FL)AK (SEQ ID NO: 87) (HLA-A*0101) and KVFPC(FL)ALINK (SEQ ID NO: 88) (HLA-A*1101) (Sette A et al), KVFPC (FL)ALINK (SEQ ID NO: 89) (HLAA*0301) (van der Burg S H et al 1995) and RYLKC(FL)QQLL (SEQ ID NO: 90) (A*2401) (Dai L C et al). B-cell lines used are: CAA (A*0101), EKR (A*0301), BVR (A*1101), VIJF (A*2401). The relative binding capacity of the peptides is expressed as the peptide concentration to inhibit 50% (1050) of the binding of the reference peptide. Affinity is categorized as follows: good IC50<5 mM, intermediate IC50=5-15 mM, and low IC50>15-50 mM. Peptide stabilization for HLA-A*0201 was performed as previously described (van der Burg S H et al, 1996). Peptides of >50% of the initial complexes was lost within 2 hours were considered unstable. Stability of other peptide-HLA complexes was determined as follows. Peptide binding was performed at 4° C. and 20° C. and 1050 were determined. Stable peptides displayed 1050 at 20° C. that deviated <2 times of the 1050 at 4° C. Peptides that displayed 1050 at 20° C. of more than twice the 1050 at 4° C. but IC50<15 mM were considered to bind with intermediate stability. The rest was designated as unstable peptide binding.

In Vitro Proteasome Mediated Digestions and Mass-Spectrometry 20S immuno-proteasomes were purified from a mouse B-cell line (RMA) and a human B-LCL cell line (JY) and 20S household proteasomes were purified from human tumor cell line (HeLa) as described (Kessler J H et al 2001). To assess kinetics, digestions were performed with different incubation periods as indicated. Briefly, peptides containing the (potential) CTL epitopes (30 mers, 20 µg) were incubated with 1 µg of purified proteasome at 37° C. for 1 h, 4 h and 24 h in 300 µl proteasome digestion buffer, trifluoroacetic acid (30 µl) was added to stop the digestion and samples were stored at −20° C. before mass spectrometric analysis. Electrospray ionization mass spectrometry was performed on a hybrid quadrupole time-of-flight mass spectromter, a Q-TOF (Micromass), equipped with an on-line nanoelectrospray interface with an approximate flow rate of 250 mL/min as described (Kessler J H et al 2001). The peaks in the mass spectrum were searched in the digested precursor peptide using the Biolynx/proteins software (Micromass) supplied with the mass spectrometer. The intensity of the peaks in the mass spectra was used to establish the relative amounts of peptides generated after proteasome digestion. The relative amounts of the peptides are given as a percentage of the total amount of peptide digested by the proteasome at the indicated incubation time. Major cleavage sites are defined as more than >1% of total digested peptide within the first hour.

Example 2

Vaccination Study with p53 Peptides in Ovarian Cancer Patients-Immunological Results in 7 Vaccinated Patients Objectives of the Trial
2.1 General Objectives
Primary objective:

To evaluate the safety and tolerability of a p53 specific "long peptide" vaccine in combination with a defined adjuvant with known mode of action (MONTANIDE™ ISA) (phase I part of the study)

To evaluate the immunogenicity of a p53 specific "long peptide" vaccine in combination with a defined adjuvant with known mode of action (Montanide ISA) (phase II part of the study)

2.2 End-Points

Primary endpoint of the phase I study is safety and tolerability

Primary endpoint of the phase II study is immunogenicity (p53 specific T cell responses)

2.3. Trial Design

A phase I/II vaccination study was performed in patients with ovarian cancer, using 10 overlapping p53 peptides in combination with an adjuvant with a sustained dendritic cell activating ability (MONTANIDE™-ISA-51). The flow chart phase is given in FIG. 3.

2.4. Patient Selection Criteria 2.4.1. Inclusion Criteria

Histological proven epithelial ovarian carcinoma

At least 4 weeks after termination of first line treatment (debulking surgery and platinum based chemotherapy)

Rising CA125 serum levels after first line treatment and no measurable disease according to the RECIST (Response Evaluation Criteria in Solid Tumours) criteria (Therasse P et al).

Rising CA125 serum levels after first line treatment with measurable disease according to the RECIST (Response Evaluation Criteria in Solid Tumours) criteria (Therasse P et al) but not willing or otherwise not fit to receive second line chemotherapy.

A rising in CA125 is known as a prognostic marker for ovarian cancer (Ferrandina G et al, Goonewardene et al and Rustin et al).

Age 18 years or older, an expected life expectancy of at least 3 months

Absence of any psychological, familial, sociological or geographical condition potentially hampering compliance with the study protocol and follow-up schedule; those conditions should be discussed with the patient before registration in the trial Before patient registration/randomization, written informed consent must be given according to Good Clinical Practice (GCP), and national/local regulations.

Performance status 0 to 2 (WHO scale)

Adequate hepatic, renal, and bone marrow function as defined:
INR <1.5; WBC >3.0×109/L; thrombocytes >100×109/L; hemoglobin >6.0 mmol/l.

2.4.2. Exclusion Criteria
Pregnancy and/or breast feeding.
Other malignancies (previous or current), except basal or squamous cell carcinoma of the skin.
High dose of immunosuppressive agents.
Prior therapy with a biological response modifier.
Uncontrolled hypertension, unstable angina pectoris, arrhythmias requiring treatment or myocardial infarction within the preceding 3 months.
Uncontrolled congestive heart failure or severe cardiomyopathy.
Signs or symptoms of CNS metastases.
Severe neurological or psychiatric disorders.

2.4.3 Withdrawal Criteria
progressive disease necessitating other forms of anti-tumor therapy
unacceptable toxicity (gr 3-4 toxicity due to vaccination persisting for more than 2 weeks)
patient refusal
lost to follow-up 2.5. Therapeutic Regimens, Expected Toxicity.

Most Th and CTL responses recognize peptides within the residues 70-251 of the p53 protein. Therefore the vaccine encompasses this region of the p53 protein. The peptides used are given in table 3.

The clinical grade peptides for vaccination are prepared in the Peptide Laboratory, section IGFL, department of Clinical Pharmacy and Toxicology, Leiden University Medical Center. Technical details on production processes or product are described in the relevant IMPD. The p53 peptides are 9 30-mers, and 1 25-mer overlapping each other by 15 residues (see table 3). This set of 10 peptides is expected to contain the possible CTL epitopes for all class I alleles as well as the possible T-helper epitopes for all class II alleles.

MONTANIDE™-ISA-51 is used as an adjuvant: MONTANIDE™ ISA 51 or purified incomplete Freund's adjuvant is composed of 10±2% (w/w) mannide oleate (MONTANIDE™ 80) in 90±2% (w/w) Drakeol 6VR, a pharmaceutical-grade mineral oil. MONTANIDE™ ISA 51 is marketed as a sterile, pyrogen-free adjuvant for human use by Seppic (Paris, France). Long term (35 years) monitoring of 18000 patients—that received incomplete Freund's adjuvanted vaccine—and 22000 controls, did not show a significant difference in death rate due to cancer: 2.18% and 2.43% for vaccines with and without adjuvant, respectively.

2.6. Dosage and Treatment Overview

A phase I vaccination study at first in 5 patients with rising CA125 levels is performed. The dose of peptides consists of 300 µg/peptide. This dose is chosen based on prior clinical trials of peptide vaccination (Rosenberg S A et al, Hersey P et al) and results from the phase I/II HPV E6/E7 long peptide trial performed at LUMC (unpublished data). Vaccination is carried out 4 times with a 3 weeks interval with clinical and immunological evaluation in between. The vaccine is injected deep subcutaneously, at four different sites, in a dose of 300 µg per peptide in DMSO/20 mM phosphate buffer pH 7.5/ MONTANIDE™ ISA-51 adjuvant. The first injection is in the right upper arm, the second in the left upper arm, the third in the left upper leg and the fourth and last in the right upper leg. Prior to vaccination, mononuclear blood cells (PBMC; stored in 10% DMSO in liquid nitrogen) and serum is isolated for evaluation of the baseline immune status towards p53 prior to vaccination. The effect of vaccination on p53 immunity is tested in PBMC and serum samples taken 2 weeks after the second- and final (booster) vaccination. T cell responses against the individual peptides in the vaccine are measured. In addition, a skin biopsy is taken from the fourth vaccination site, 2 weeks after vaccination, to isolate infiltrating T-cells. These T-cells are tested with respect to their specificity and polarization.

If no grade 3 or 4 toxicity occurs in any of the 5 patients entered in the phase I study the phase II vaccination study is started. If one patient experiences unexpected grade 3 or 4 toxicity, the number of patients in the phase I will be expanded to 10. It should be noted that in previous peptide vaccination studies no or minor toxicity occurred. Due to the relative good general condition normally encountered in these patients, this patient group is ideal to test the immunogenicity of the vaccine in a classical phase II trial. At first 14 patients are entered in this phase II study. P53 specific T cell responses before and after vaccination are compared. If no responders (response arbitrarily defined as >30% increase p53 specific T cell responses) are found among the first 19 patients the study is discontinued because of apparent lack of immunogenicity of the vaccine. In case of responses the total number of patients in the study depends on the number of observed responses.

Vaccination in the phase I/II study is started 3 months after the last first line chemotherapy course and continued for a total of 4 vaccinations spaced by 3 weeks. If the phase II vaccination shows no results in terms of positive T cell responses, this approach will be discontinued.

2.7. Supportive Care in Case of Toxicity

In case of skin toxicity, systemic antihistamines or topical steroids are allowed. Patients are not allowed to receive growth factors for myelosuppression. Analgetics are allowed.

2.8. Concomitant Therapy

No other chemotherapy, immunotherapy, hormonal agents (excluding topical steroids for skin rashes), radiation therapy, experimental drugs, radiotherapy, and/or surgery are allowed while patients are on study. Any disease progression necessitating other forms of anti-tumor therapy is a cause for patient's withdrawal from the study. Systemic corticosteroids are not permitted during the study. Patients should receive full supportive care.

2.9 Clinical Evaluation, Laboratory Tests and Follow-Up 2.9.1 Before Treatment Start Less than 14 days before registration within the trial the following parameters are required to recorded:
relevant medical history including date of first diagnosis, histological type, concurrent diseases, and any concurrent use of medication.
Physical examination including WHO performance, height, weight, vital signs, base-line clinical symptoms.
Electrocardiogram (ECG) and urine analysis to exclude an asymptomatic cystitis
Hematology: hemoglobin, thrombocytes, WBC.
Biochemistry: serum creatinine, INR, bilirubin, ASAT, ALAT, LDH,
When the patient is registered within the trial, study treatment starts within 7 days after inclusion.

2.9.2. During Treatment

Less than 28 days before start of vaccination (300 ml), during vaccination (3×50 ml) and approximately 14 days after the last vaccination (300 ml) PBMC are collected to measure p53 specific T cell responses.

Two weeks after the last vaccination a punch biopsy is taken from the fourth vaccination site.

Immediately before administration of each vaccination, 10 to 14 days after the last administration of the vaccine, the following examinations are carried out: (1) physical examination including neurological evaluation, vital signs, $O_2$-saturation and ECG before and three-four hours after each vaccination. (2) Evaluation of all adverse events (worst grade of events occurring during this vaccination should be recorded), as well as weight and WHO performance, (3) Hematology and biochemistry including hemoglobin, thrombocytes, WBC, serum creatinine, INR, bilirubin, ASAT, ALAT, LDH and INR. (4) Any concomitant medication.

2.9.3. After the End of Treatment (Follow-Up)

If the patient has not progressed after vaccination, the extent of disease is recorded every 3 months following the same procedures as during treatment. In case of progression, the patients are followed for survival every 3 months. Initiation of any form of other anti-tumor treatment is recorded. Table 4 summarizes the whole vaccination and analysis process.

Toxicity evaluation is recorded during vaccination. Hematology and biochemistry including hemoglobin, thrombocytes, WBC, serum creatinine, INR, bilirubin, ASAT, ALAT, LDH and INR.

2.10. Immuno-Monitoring

At five different time points during the study PBMC are collected: before vaccination (300 ml), and after each vaccination (3×50 ml) and after the last vaccination (300 ml). PBMC and serum is isolated.

Evaluation of the p53-specific T cell responses in vaccinated subjects of the phase I/II study is carried out as follows:

Positive CD4+ T helper cell responses after vaccination are defined by:

a) Significantly increased (a vaccination induced reaction is considered positive when the proliferation index of post-vaccination samples is at least twice as high as the proliferation index of pre-vaccination samples and the proliferation index of post-vaccination samples should at least be 2 and/or b) Significantly increased IFNγ production of PBMC, that have been stimulated twice with peptide in vitro, against p53 peptides as measured by ELISA following 1 day culture, and/or c) A significantly increased percentage of CD4+ PBMC that produce IFNγ upon a 6 hour in vitro stimulation with p53 peptides in the presence of brefeldin A, utilizing tricolor intracellular FACS staining with antibodies against CD4, the early activation marker CD69 and IFNγ, and/or d) A significantly increased number of antigen-specific T cells that produce IFNγ, IL-4 or IL-10 as measured in the ELISPOT assay in which a frequency of $\geq 1/10,000$ PBMC is considered positive and a twofold increase in the number of spots between pre-vaccination and post-vaccination is chosen as a positive response to the vaccine.

2.11. Statistical Consideration 2.11.2. Analysis

Patients not satisfying the inclusion criteria are ineligible. Patients not evaluated because of withdrawal or for other reasons (e.g. patients refusal, lost to follow-up, protocol violation) are clearly indicated. A total of 19 full evaluable patients need to be entered in the study with a maximum of 20% drop-out, this number might increase to 23 patients).

The p53 specific immune response of the vaccine measured before and after the vaccinations will be compared by Sign test (2-sided, 5% significance level). Response rates and rates of grade 3-4 toxicity encountered during vaccination will be estimated and the 95% exact confidence limits calculated. Time to progression will be computed by Kaplan-Meier curves and will be compared to a historical control group by the logrank test.

2.12. Translational Research

The following analyses are performed:

The p53-specific T-cell response is analyzed using freshly isolated PBMC for p53-specific proliferation. The cytokines (IFNγ, TNFα, IL-10, IL-5, IL-4, IL-2) that are specifically produced upon this antigenic stimulation are tested by the cytokine bead array (according to the protocol of the manufacturer Becton-Dickinson). PBMC freshly isolated before, during and after the fourth vaccination, are tested. Responses are classified as Th1 (IFNγ, TNFα), Th2 (IL-4, IL-5, IL-10), Th0 (IFNγ, IL-4, IL-5, IL-10) or impaired with respect to cytokine production (no production).

The presence of high numbers of p53-specific T-cells in the peripheral blood may not in all cases lead to the migration of these T-cells to the vaccine injection site, despite the presence of peptide antigen. The success or failure of T-cells to migrate into the skin may be a reflection of what goes on at the site of disease. Therefore, 2 weeks after the last vaccination a biopsy is taken from the fourth vaccination site. T-cells that have infiltrated the vaccination site are isolated from the biopsy. The specificity, polarization and type of the infiltrating T-cells is tested by cytokine bead array (protocol of manufacturer) and by FACS.

2.13. Results 2.13.1. Proliferation Assay

FIG. 4 depicts the proliferation assay carried out as indicated. It demonstrates that the vaccine containing peptides covering $p53_{70-248}$ is able to induce an immune response in most patients. Clearly, peptides derived from the region of $p53_{102-248}$ most efficiently induce a T cell response after vaccination as measured by proliferation after in vitro stimulation with pools of vaccine peptides (FIG. 4b-d). The first pool of vaccine peptides, covering $p53_{70-101}$, hardly induces T cell proliferation after in vitro stimulation (FIG. 4a). T cells isolated from vaccinated patients were also stimulated with peptides that were not present in the vaccine. This concerned peptides covering the N-terminal and the C-terminal region of the p53 protein. As shown by FIG. 4f, the N-terminal region is able to induce a T cell response in some ovarian cancer patients. This could indicate that the vaccine is very efficient at inducing killer T cells, eventually resulting in epitope spreading. On the other hand, the C-terminal region of p53 in these patients does not induce a measurable T cell response.

2.13.2. IFNγ ELISPOT

The vaccine was considered to induce a positive response if:

the mean number of spots–(mean number of spots in medium+2SD)>10 spots post-vaccination SI>=twice the prevaccination SI. The results are depicted in FIG. 6.

Figure 6A:
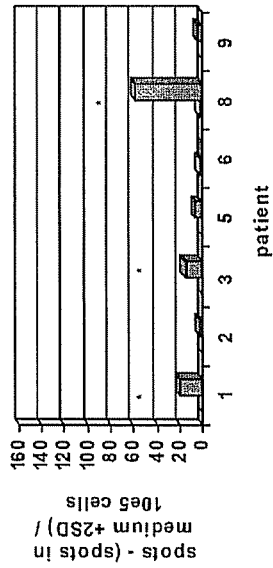
FIG. 6. P53-peptide specific responses as measured by IFN-γ ELISPOT (n=7) in ovarian cancer patients.
Figure 6B:
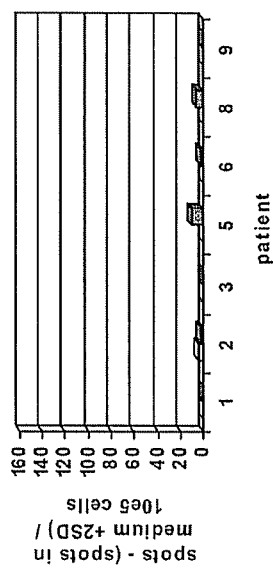
Figure 6C:
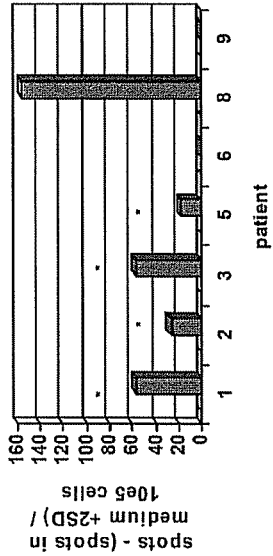
Figure 6D:
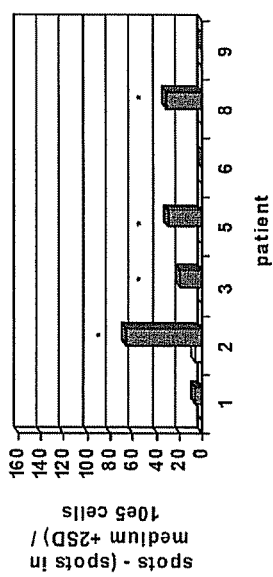
Figure 7B:
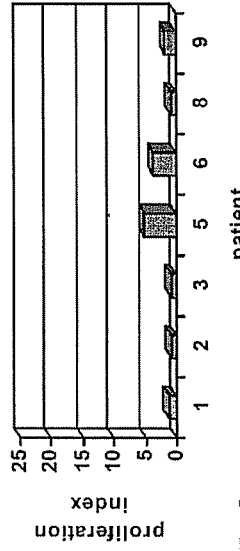
Figure 7D:
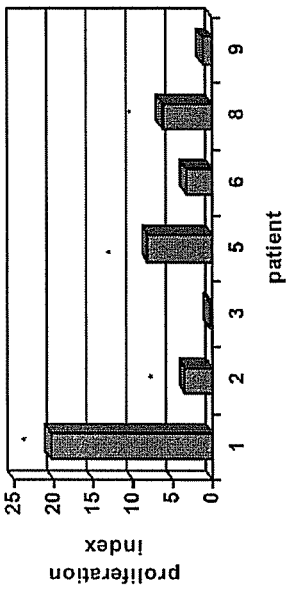
Figure 7A:
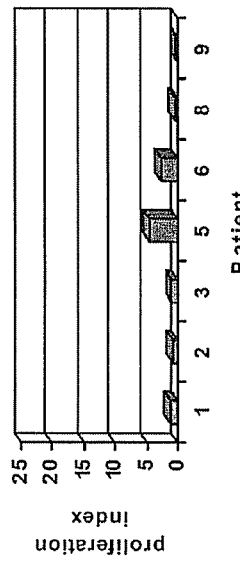
Figure 7C:
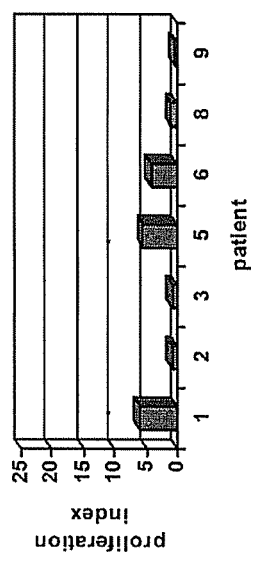

This assay shows similar results compared to the proliferation assay: The vaccine peptides derived from the $p53_{102-248}$ region have induced T cells specific for epitopes contained in that area (FIG. 6b-d), whereas the peptides derived from the $p53_{70-101}$ region do not (FIG. 6a). Moreover, this assay further confirms that the principal of epitope spreading might take place in some patients (FIG. 6f).

Example 3

Figure 3:
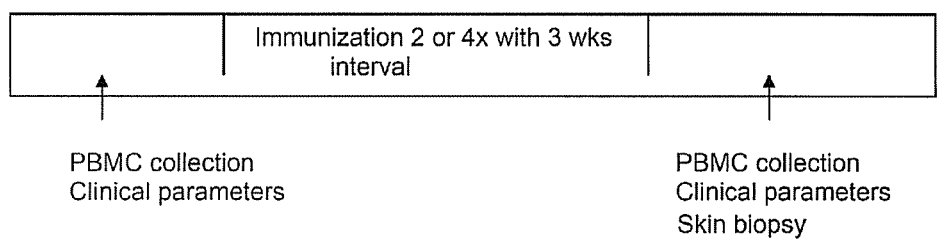
FIG. 3. Flow chart of phase I and II of the clinical trial in ovarian cancer patient as presented in example 2 and in colon cancer patient as presented in example 3. For ovarian cancer patient, fours shots of vaccine are used, whereas for colon cancer patient, two shots of vaccine are used. For colon cancer patient, the skin biopsy was carried out at the second vaccine site.
Figure 4B:
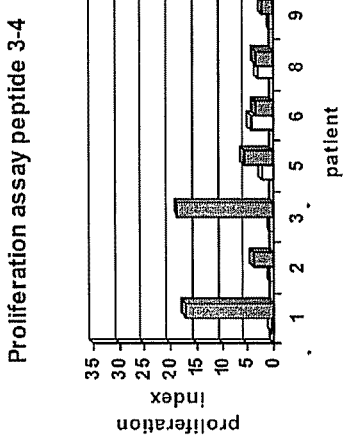
FIG. 4. P53-peptide specific responses in clinical trial of ovarian cancer patients as measured by proliferation assay (n=8).A-F) Vaccine induced response (*) if post-vaccination sample ≥1000 cpm & proliferation index ≥3 and if post-vaccination cpm value ≥2× pre-vaccination cpm value. G) Responses to memory recall mix (MRM). Light grey bars: pre-vaccination, black bars: post-vaccination.
Figure 4D:
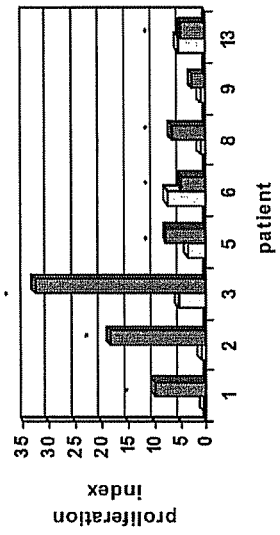
Figure 4A:
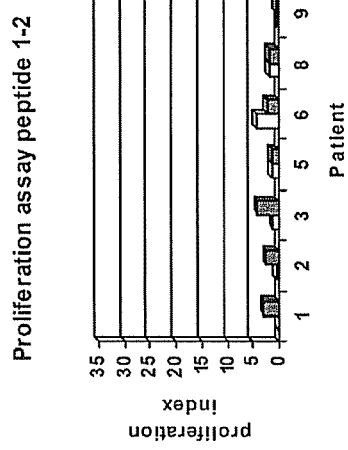
Figure 4C:
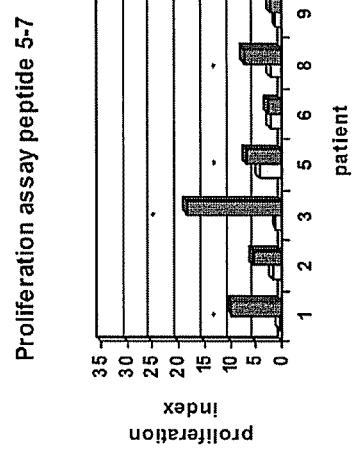
Figure 4E:
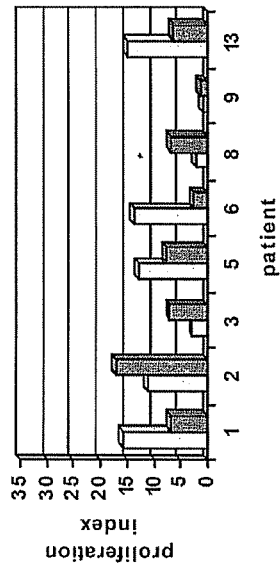
Figure 4F:
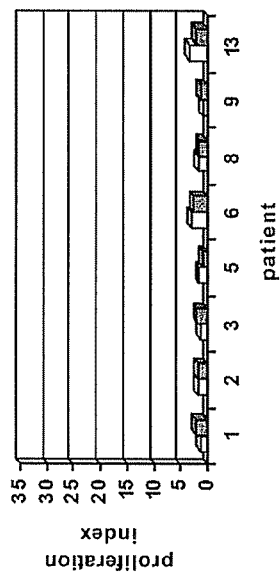
Figure 4G:
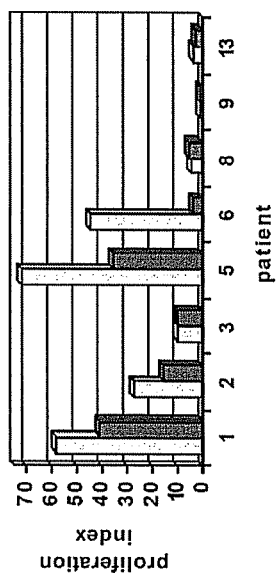

Vaccination Study with p53 Peptides in Colorectal Cancer Patients-Immunological Results in 2 Vaccinated Patients The principle of the study is similar as in example 2 (see also FIG. 3). The differences being that in this study, patients only received two vaccinations (instead of four).

Figure 5A:
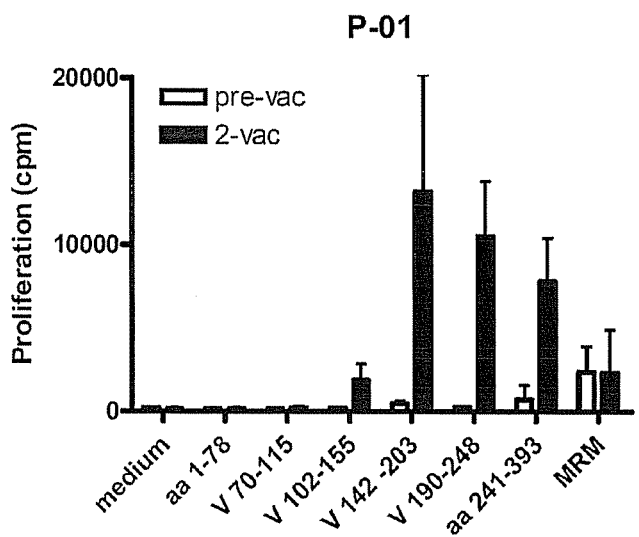
FIG. 5. P53-peptide specific responses in clinical trial of colon cancer patients as measured by proliferation assay and cytokine production. The p53-specific proliferative capacity (A and C) and cytokine production (B and D) of 2 male patients with colorectal cancer is shown before and after vaccination with p53-long peptide vaccine. Patients were vaccinated twice with overlapping p53 peptides covering the amino acid sequence 70-248 (indicated by the pools of 2 peptide: V70-115, V102-155, V142-203, V190-248). Patients PBMC were also tested against the N-terminal region of p53 (aa 1-78) and C-terminal region of p53 (aa 241-393).
Figure 5B:
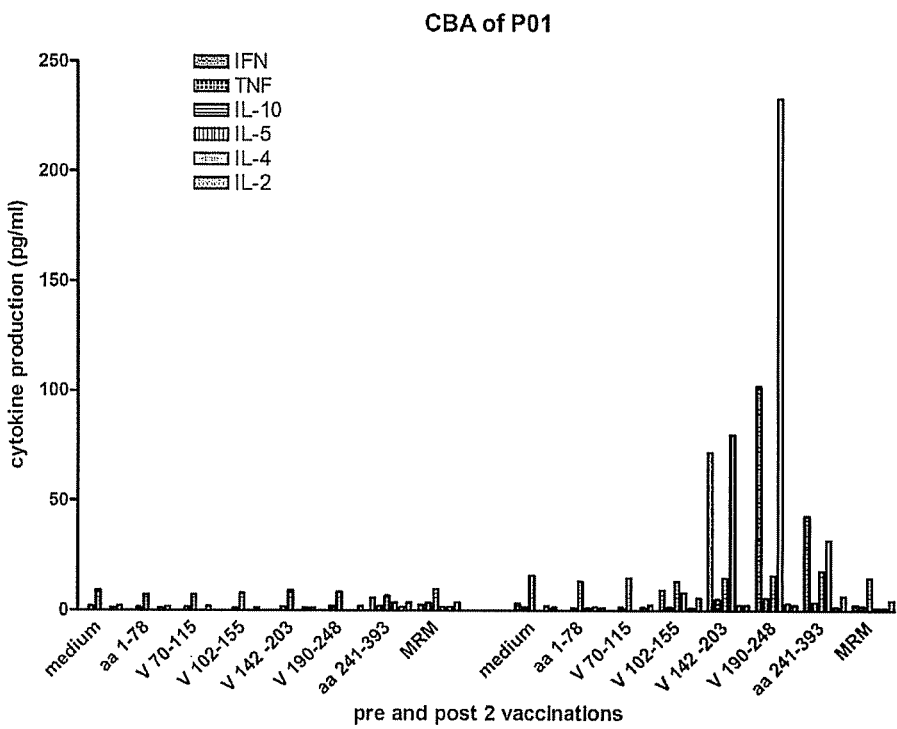
Figure 5C:
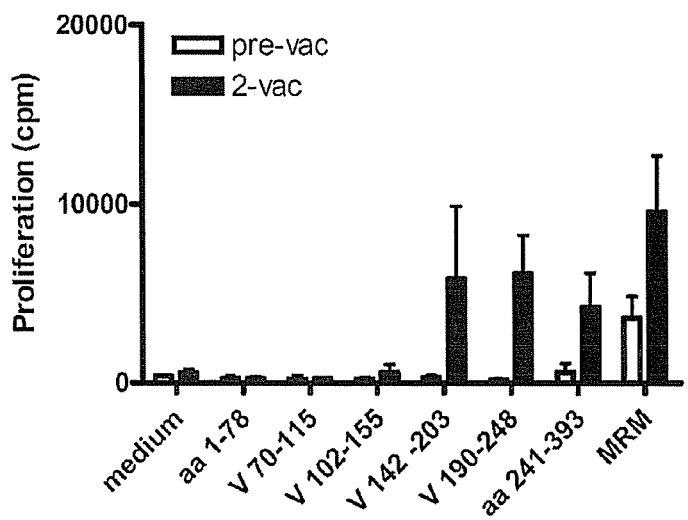
Figure 5D:
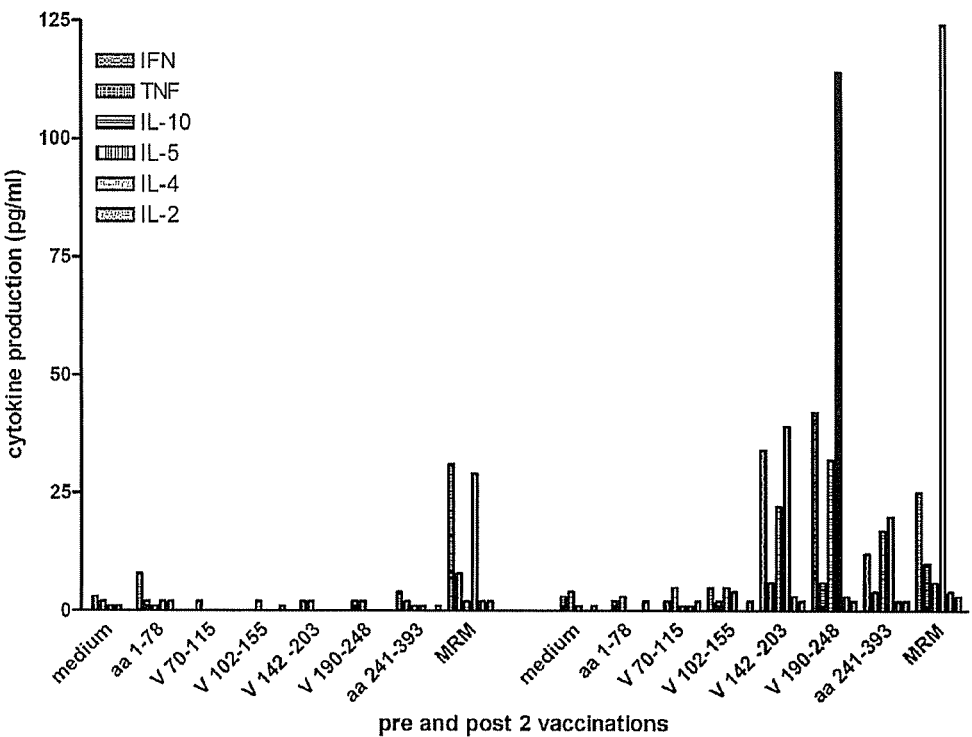

The p53-specific proliferative capacity (FIGS. 5A and C) and cytokine production (FIGS. 5B and D) of 2 male patients with colorectal cancer is shown before and after vaccination with p53-long peptide vaccine. Patients were vaccinated twice with overlapping p53 peptides covering the amino acid sequence 70-248 (indicated by the pools of 2 peptide: V70-115, V102-155, V142-203, V190-248). Patients PBMC were also tested against the N-terminal region of p53 (aa 1-78) and C-terminal region of p53 (aa 241-393). Note that in both cases, vaccination results in the activation of T-cell reactivity against the C-terminal region (outside the vaccine) too, indicative for epitope-spreading of the immune response following vaccination. P53-specific proliferation is associated with the production of IFNγ, IL-10 and IL-5, as measured by Cytokine bead Array (CBA).

Example 4

Vaccination Study with p53 Peptides in Colorectal Cancer Patients-Immunological Responses in 9 Vaccinated Patients Table 6 shows an overview of p53 specific T cell responses in colorectal cancer patients that have been vaccinated twice with the p53 SLP vaccine. In conclusion, all patients exhibited a p53 specific T cell response. The peptides that seem to be the most immunogenic are located in the most N-terminal portion of the p53 protein as present in the vaccine (aa 190-248): 8 out of 9 patients responded against these peptides. However, also peptides derived from aa 102-155 and 142-203 are able to induce p53 specific responses (6 out of 9 patients respond to one or more peptides derived from these regions). Clearly, the C-terminal portion of p53 seems to be less immunogenic. Importantly, peptides derived from the N-terminal portion of p53 which was not present in the p53 SLP vaccine still were able to induce a T cell response in vitro. This phenomenon is known as antigen spreading and occurs through stimulation of T-cells by DC that have taken up tumor-derived p53 released by dying tumor cells. As this is observed after vaccination only it is indicative for an effective vaccine-induced anti-tumor response.

To determine whether the p53 SLP vaccine is able to induce p53 specific T cells that can migrate to areas where the p53 antigen is presented, vaccine sites were isolated and skin-infiltrating T cells were expanded. FIG. 8 shows the results from 1 patient with colorectal cancer. T cells have migrated to the vaccine site and are mostly specific for vaccine peptides 5-10 (aa 142-248). Furthermore, also peptides encoding the N-terminal portion of the p53 protein (aa 241-393) can be recognized by infiltrating T cells, while this part of the protein is not present in the p53-SLP vaccine. Again evidence for antigen spreading after effective vaccination. Importantly, the results also show that vaccine induced T cells that have migrated to the area of antigen presentation can also recognize cells that have processed whole p53 protein. This indicates that the natural processing pathway processes p53 protein into epitopes that can be recognized by the vaccine induced T cells. This implies that tumor cells that also process whole p53 protein in a natural manner can also be recognized and lysed by these T cells.

To determine whether the vaccinated colon carcinoma patients were also able to induce a memory T cell response, PBMC isolated before and after 2 vaccinations and after 6 or 9 months were tested for the presence of p53 specific T cells. In FIG. 9, shows that the p53-specific T-cell responses which were not present before vaccination and induced after 2 vaccinations were still present in the circulation of the tested patients at 6-9 months after vaccination which is indicative for p53-specific memory T-cell responses. Moreover, both patients display a response to amino acids 241-393 of the p53-protein after 2 vaccinations and even at 6 months of follow up (#1), indicating that T cells induced as a result of epitope spreading were also still present.

Example 5

Vaccination Study with p53 Peptides in Ovarian Cancer Patients-Immunological Results in All (18) Vaccinated Patients Table 7 summarizes immunological and clinical responses of all ovarian cancer patients treated with the p53-SLP vaccine.

Immunological Responses

In 100% of the ovarian cancer patients receiving all four immunizations (N=18), vaccine-induced p53-specific responses against the vaccine peptides were present at two or more time points (I-IV) after immunization as measured by IFN-γ ELISPOT (Table 8). Vaccine-induced p53-specific responses were directed against at least two of the vaccine peptide pools in all ovarian cancer patients. After four immunizations, circulating IFN-γ secreting p53-specific T-cells could be detected in 61.1% (11/18) of patients.

Vaccine-induced p53-specific proliferative responses against the vaccine peptides were observed in 82.4% (14/17) of ovarian cancer patients (Table 9). As depicted in FIG. 12, proliferative responses against the vaccine peptides could still be demonstrated 9-12 months after the last immunization, even though patients had since been treated with chemotherapy. Furthermore, also in the ovarian cancer patients, p53-specific responses against the first (aa 1-78) and the last (aa 241-393) portion of the p53-protein not covered by the vaccine peptides, were observed in 11.8% (2/17) and 23.5% (4/17) of the patients respectively after four immunizations (Table 9). FIG. 10 illustrates the proliferative capacity of PBMC in response to ex-vivo stimulation with single vaccine peptides as analyzed in 7 patients with ovarian cancer after four immunizations. Responses were observed to all peptides, except for vaccine peptide 1 (aa70-99). To analyze the capacity of p53-specific T-cells to migrate to sites where p53 antigen is presented, a proliferation assay was performed with lymphocytes cultured from skin biopsies taken at the fourth injection site (n=17). Insufficient numbers of lymphocytes could be cultured from the skin biopsies of two patients (P15 and P20). P53-specific responses were observed in lymphocytes cultured from skin biopsies in 52.9% (9/17) of patients. Most responses were observed against vaccine peptide p8-p10 (aa 190-248) (FIG. 11). Importantly, all patients with p53-specific responses in lymphocytes cultured from skin biopsies also showed vaccine-induced p53-specific responses in PBMC as analyzed by proliferation assay (Table 7), although responses were not always directed against the same epitopes.

P53-autoantibodies were present in 40% (8/20) of the patients before immunization. After one or more immunizations, p53-autoantibodies were present in 45% (9/20) of patients. A vaccine-induced increase in p53-autoantibody titer was detected in 15% (3/20) of the patients (Table 7).

Clinical Responses

Because of rapidly progressive disease, two patients received only two immunizations (P04, P12). Clinical responses of the remaining 18 ovarian cancer patients were evaluated based on CA-125 levels and evaluation of CT scans according to the RECIST and GCIG criteria (Table 10). One patient had a partial response as measured by CA-125 (P05), and six patients had stable CA-125 levels (P02, P03, P06, P09, P17, P21, P23) (FIG. 13). Two of these patients (11.1%) also had stable disease on CT-scan (P17, P23). In both patients, vaccine-induced p53-specific responses were detected in PBMC. P23 also showed p53-specific responses in lymphocytes cultured from the skin biopsy. The other patients (16/18; 88.9%) were classified as having progressive disease. All patients with progressive disease had developed new lesions since their last CT-scan.

Example 6

Demonstration of the Advantage of Intradermal Administration of a Vaccine Peptide In this example, peptides were derived from a HPV protein are used in an intradermal vaccine. The advantages of an intradermal vaccine as demonstrated herein are generalisable to any other peptides, among other derived from a protein that is ubiquitously expressed self-antigen and known to be associated with cancer, such as p53.

Materials and Methods
Study Design

A cross-sectional pilot study to analyse HPV16 E2-, E6-, and E7-specific T-cell responses as measured by intradermal injection of pools of clinical grade HPV16 peptides in the upper arm was performed in patients with HPV-related disorders of the cervix and in healthy individuals. Since a delayed type hypersensitivity reaction represents a memory T-cell response, there was no prerequisite for HPV16-positivity at the time of analysis.

Subjects

A group of nineteen healthy individuals (HD) participated in this study after providing informed consent. The group of healthy individuals displayed a median age of 31 years old (range, 20-51 years) and was comprised of 80% women and 20% males. Peripheral blood mononuclear cells (PBMCs) were obtained from all subjects immediately before administration of the skin test. The late appearance of positive skin tests in healthy individuals resulted in the isolation of a second blood sample from 11 of 19 healthy volunteers. The study design was approved by the Medical Ethical Committee of the Leiden University Medical Centre.

DTH Skin Test

Skin tests, based on Delayed Type Hypersensitivity reactions (DTH), can be used as a sensitive and simple method for in vivo measurement of HPV-specific cellular immune responses (Hopfl R et al, 2000; Hopfl R et al, 1991). The skin test preparations consisted of 8 pools of long clinical-grade synthetic peptides spanning the whole HPV 16 E6 and E7 protein and the most immunogenic regions of HPV 16 E2 protein (de Jong A et al, 2004). These clinical grade peptides were produced in the interdivisional GMP-Facility of the LUMC. Each pool of the skin test consisted of 2 or 3 synthetic peptides, indicated by the first and last amino acid of the region in the protein covered by the peptides. Pool 1: $E2_{31-60}$, $E2_{46-75}$, Pool 2: $E2_{301-330}$, $E2_{316-345}$, Pool 3: $E6_{1-31}$, $E6_{19-50}$, Pool 4: $E6_{41-65}$, $E6_{55-80}$, $E6_{71-95}$, Pool 5: $E6_{85-109}$, $E6_{91-122}$, Pool 6: $E6_{109-140}$, $E6_{127-158}$, Pool 7: $E7_{1-35}$, $E7_{22-56}$, Pool 8: $E7_{43-77}$, $E7_{64-98}$. The sequence of E2, E6, and E7 of HPV16 is respectively represented by SEQ ID NO:22, 23, and 24. Per peptide pool 0.05 ml of 0.2 mg/ml peptides in 16% DMSO in 20 mM isotonic phosphate buffer (10 µg/peptide) was injected intracutaneously. The pools of peptides and a negative control (dissolvent only) were injected separately at individual skin test sites of the upper arm. Skin test sites were inspected at least three times, at 72 hours and 7 days after injection (Hopfl R et al 2000, 2001) of the peptides and at 3 weeks following the first report of a very late skin reaction in one of the first healthy subjects. Reactions were considered positive when papules greater than 2 mm in diameter arose no less than 2 days after injection. From positive skin reaction sites punch biopsies (4 mm) were obtained, cut in small pieces and cultured in IMDM containing 10% human AB serum, 10% TCGF and 5 ng/ml IL7 and IL15 to allow the emigration of lymphocytes out of the skin tissue. After 2 to 4 weeks of culture the expanded T cells were harvested and tested for their HPV-specific reactivity.

Antigen for In Vitro Immune Assays

A set of peptides, similar to the peptides used in the skin test, were used for T—cell stimulation assays and IFNγ-ELISPOT assays. The four HPV 16 E2 peptides consisted of 30-mer peptides overlapping 15 residues, HPV 16 E6 consisted of 32-mers and HPV 16 E7 of 35-mers, both overlapping 14 residues. The peptides were synthesized and dissolved as previously described (van der Burg S H et al, 1999). Notably, in the IFNγ ELISPOT assays peptide pool 4 and 5 slightly differed from the peptide pools used in the skin test, pool 4 contained peptides $E6_{37-68}$, $E6_{55-86}$, $E6_{73-104}$ and pool 5 comprised peptides $E6_{73-104}$, $E6_{91-122}$.

Memory response mix (MRM 50×), consisting of a mixture of tetanus toxoid (0.75 Limus flocculentius/ml; National Institute of Public Health and Environment, Bilthoven, The Netherlands), *Mycobacterium tuberculosis* sonicate (5 µg/ml; generously donated by Dr. P. Klatser, Royal Tropical Institute, Amsterdam, The Netherlands), and *Candida albicans* (0.15 mg/ml, HAL Allergenen Lab., Haarlem, The Netherlands) was used as a positive control. Recombinant HPV 16 E2, E6 and E7 proteins were produced in recombinant *Escherichia coli* as described previously (van der Burg S H et al, 2001).

Analysis of Antigen-Specific Th Cells by IFNγ ELISPOT

The presence of HPV 16-specific Th Cells was analyzed by ELISPOT as described previously (van der Burg S H et al, 2001) Briefly, fresh PBMCs were seeded at a density of $2 \times 10^6$ cells/well of a 24-well plate (Costar, Cambridge, Mass.) in 1 ml of IMDM (Bio Whittaker, Verviers, Belgium) enriched with 10% human AB serum, in the presence or absence of the indicated HPV 16 E2, E6 and E7 peptide pools. Peptides were used at a concentration of 5 µg/ml/peptide. After 4 days of incubation at 37° C., PBMCs were harvested, washed, and seeded in four replicate wells at a density of $10^5$ cells per well in 100 µl IMDM enriched with 10% FCS in a Multiscreen 96-well plate (Millipore, Etten-Leur, The Netherlands) coated with an IFNγ catching antibody (Mabtech AB, Nacha, Sweden). Further antibody incubations and development of the ELISPOT was performed according to the manufacturer's instructions (Mabtech). Spots were counted with a fully automated computer-assisted-video-imaging analysis system (Bio Sys). Specific spots were calculated by subtracting the mean number of spots+2×SD of the medium control from the mean number of spots in experimental wells (van der Burg S H et al, 2001).

T Cell Proliferation Assay

T-cell cultures of the skin biopsies were tested for recognition of the specific peptides and protein in a 3-day proliferation assay (van der Burg S H et al, 2001). Briefly, autologous monocytes were isolated from PBMCs by adherence to a flat-bottom 96-well plate during 2 h in X-vivo 15 medium (Cambrex) at 37° C. The monocytes were used as APCs, loaded overnight with 10 µg/ml peptide and 20 µg/ml protein. Skin test-infiltrating-lymfocytes were seeded at a density of 2-5×10$^4$ cells/well in IMDM suplemented with 10% AB serum. Medium alone was taken along as a negative control, phytohemagglutinine (0.5 µg/ml) served as a positive control. Proliferation was measured by [$^3$H]thymidine (5 µCi/mmol) incorporation. A proliferative response was defined specific as the stimulation index (SI)≥3. Supernatants of the proliferation assays were harvested 48 hours after incubation for the analysis of antigen-specific cytokine production.

Analysis of Cytokines Associated with HPV16-Specific Proliferative Responses

The simultaneous detection of six different Th1 and Th2 cytokines: IFNγ, tumor necrosis factor α, interleukin 2 (IL2), IL4, IL5 and IL 10 was performed using the cytometric bead array (Becton Dickinson) according to the manufacturer's instructions.

Cut-off values were based on the standard curves of the different cytokines (100 pg/ml IFNγ and 20 pg/ml for the remaining cytokines). Antigen-specific cytokine production was defined as a cytokine concentration above cutoff level and >2× the concentration of the medium control (de Jong A et al, 2004).

Intracellular Cytokine Staining (ICS)

The specificity and character of the T cell cultures derived from positive skin reaction sites was tested by ICS as reported previously (de Jong A et al, 2005). Briefly, skin test infiltrating lymphocytes were harvested, washed and suspended in IMDM+10% AB serum and 2-5×10$^4$ cells were added to autologous monocytes that were pulsed overnight with 50 µl peptide (10 µg/ml) or protein (20 µg/ml) in X vivo medium. Medium alone was taken along as a negative control, phytohemagglutinine (0.5 µg/ml) served as a positive control. Samples were simultaneously stained with FITC-labelled mouse-antihuman IFNγ (0.5 g/ml, BD PharMingen), PE-labelled mouse-antihuman IL5 (0.2 mg/ml, BD PharMingen), APC-labelled anti-CD4 (BD Bioscience) and PerCP-labelled anti-CD8 (BD Bioscience). After incubation at 4° C., the cells were washed, fixed with 1% paraformaldehyde and analyzed by flow cytrometry (Facsscan, Bd Biosciences)

Statistical Analysis

Fisher's Exact test (2-tailed) was used to analyze the relationship between the detection of IFNγ-producing HPV-specific T-cells in PBMC, the presence of a skin test reaction or the presence of HPV-specific T-cells in skin biopsies, as well as differences between patients and healthy controls with respect to the size or the number of the skin reactions within these groups. Statistical analyzes were performed using Graphpad Instat Software (version 3.0) and Graphpad Prism 4.

Results

Skin Reactions to Intracutaneous Injection with HPV 16 E2, E6- and E7 Peptides

Figure 14:
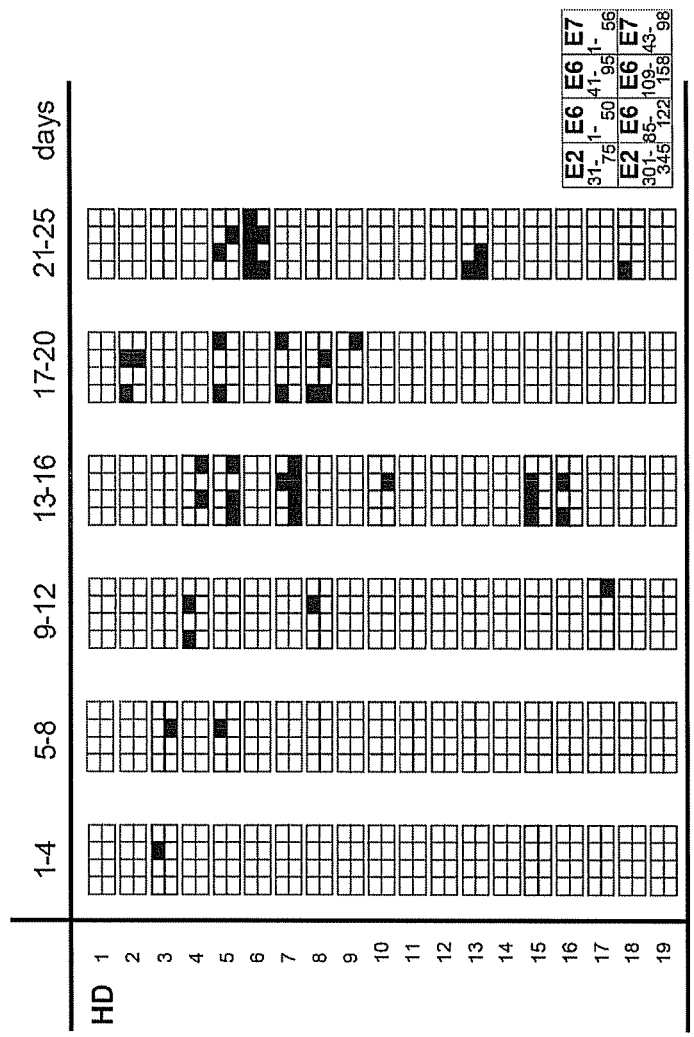

We studied skin reactions in healthy subjects after intracutaneous injection with HPV16 E2, -E6 and -E7 peptides. Positive skin reactions appeared as flat reddish papules of 2 to 20 mm of diameter, arising within 2 to 25 days after injection. A positive skin reaction was detected in 46 of the 152 skin tests in the healthy volunteers. Over all, each peptide-pool in the skin test could give rise to a positive skin reaction. Most frequently reactions against E2$_{31-75}$ (10 out of 19 subjects), E6$_{37-104}$ (9/16) and E7$_{43-98}$ (7/19) were observed in the control group. This reaction pattern resembles that of what we previously observed in PBMC (de Jong A et al, 2002; Welters et al, 2003) (FIG. 14). These skin reactions corresponded with the presence of a peptide specific T cell response as detected in the PBMC of these individuals (data not shown).

Skin Reactions in Healthy Donors are Associated with Higher Frequencies of HPV 16-Specific T-Cells in the Peripheral Blood.

In order to compare the results of the skin test with the presence of circulating HPV 16-specific type 1 T cells, an IFNγ ELIspot assay was performed with PBMC's collected before the intradermal peptide-challenge was given. In 5 out of 19 healthy volunteers we were able to detect a HPV 16-specific immune response by IFNγ-ELIspot. The detection of ≥5 circulating HPV 16-specific T-cells per 100.000 PBMC in the pre-challenge blood sample of healthy individuals was associated with an early (≤13 days) positive skin reaction to the same peptide sequence (p=0.0003, two tailed Fisher's exact test; FIG. 15). No HPV16-specific circulating T-cells were detected in the pre-challenge blood sample healthy donors to peptides that induced a late positive skin reaction (14 to 25 days). This suggests that the frequency of circulating antigen-specific cells determine the delay time for skin reactions to appear.

In order to assess the frequency of HPV-specific T-cells at the time that a late skin reaction appeared additional blood samples from 11 healthy volunteers were collected. In these individuals 39 out of 88 skin tests were positive. In 25 of the 39 positive skin reactions and in 10 of 49 negative skin reactions ≥5 HPV 16-specific T-cells were detected per 100.000 PBMC. At this point a significant correlation was found between the detection of circulating HPV-specific IFNγ-producing T-cells in the post-challenged blood sample and the presence of a skin reaction (p<0.0001, Fisher's exact test; FIG. 16). This shows that the frequency of HPV16-specific T cells in the blood of healthy volunteers is significantly higher following an intradermal challenge with HPV16 peptide and indicates that intracutaneous injection of peptide antigens enhances the number of HPV16-specific T cells in the blood of healthy volunteers.

Biopsies of Positive Skin Reaction Sites Consist of Both Th1/Th2− CD4+ and CD8+ HPV16-Specific T Cells.

Approximately 25% of the positive skin reactions of healthy volunteers were not associated with the detection of HPV16-specific IFNγ-producing T-cells in the blood, suggesting that other, non IFNγ-producing types of T-cells may infiltrate the skin after intradermal injection of HPV16 peptides.

Figure 17:
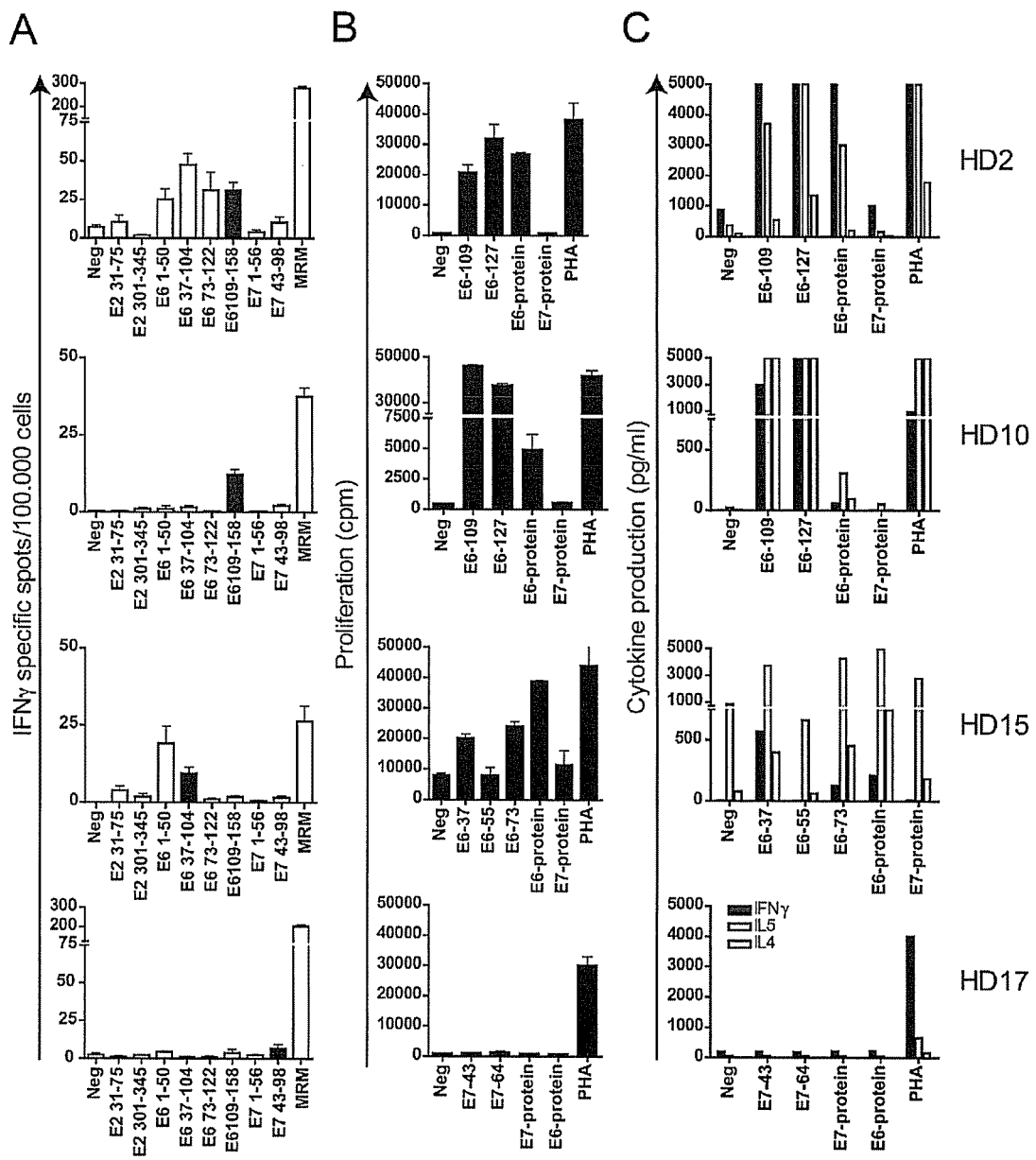

In order to characterize the cells in a positive skin reaction site punch biopsies were taken. In total, 8 biopsies were taken from different positive skin reaction sites of 7 healthy controls and cultured with a cocktail of cytokines that allowed the outgrowth of T-cells in vitro without antigenic stimulants. In 7 of 8 cases, T-cells ex-filtrated the tissue and expanded within 3-4 weeks. The expanded T-cells were tested for their specificity in a short term proliferation assay. FIG. 17 shows examples of T-cell cultures that specifically proliferated upon stimulation with autologous monocytes pulsed with the pool of peptides, also injected in this site during the skin test (HD2, HD10, HD15) as well as to monocytes pulsed with HPV16 E6 protein (FIG. 17AB). This indicates that these T-cells were capable of recognizing their cognate HLA-peptide complexes after the antigen was naturally processed and presented. Analysis of the supernatants of these proliferative T-cell cultures revealed a mixed Th1/Th2 cytokine profile in that the HPV16-specific T-cells produced IFNγ, IL-4 and IL-5 (FIG. 17C).

Figure 18:
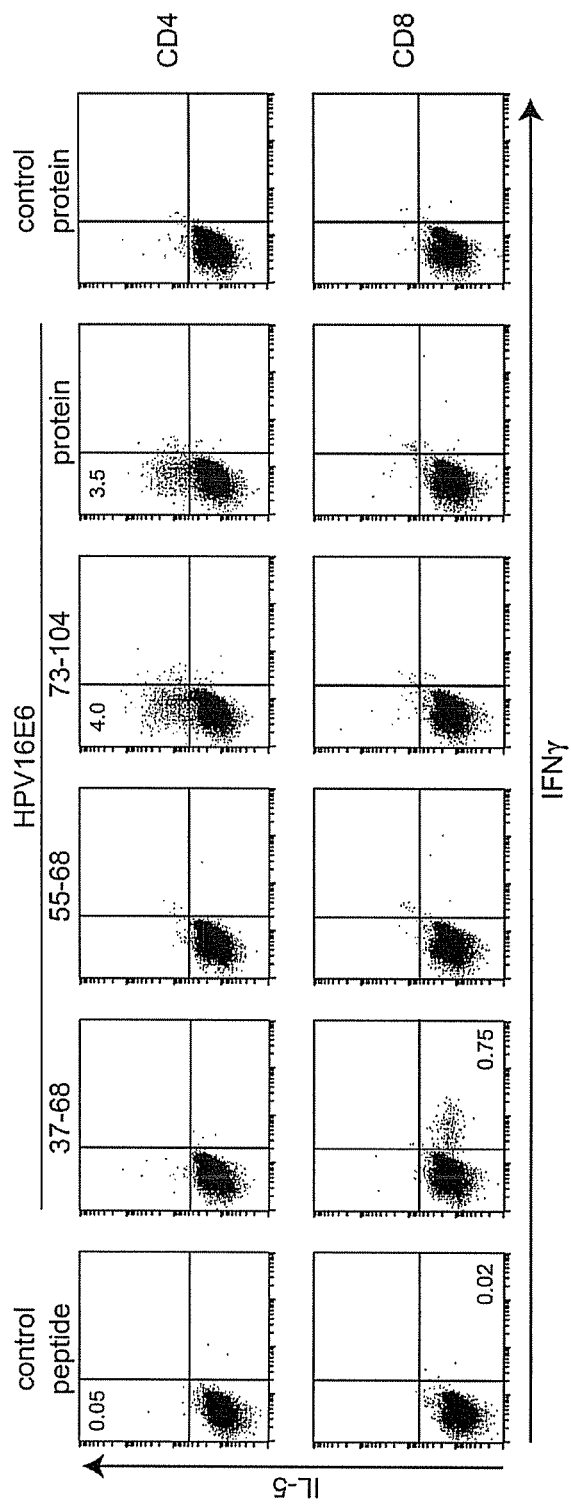

In each case that HPV-specific T-cells were detected in the biopsy culture (4 out of 8) this coincided with the detection of circulating HPV16-specific IFNγ-producing T-cells in the post-challenge blood sample by ELIspot (compare FIGS. 17A and B). In 3 of the other 4 positive skin reaction biopsies (HD2, HD17, HD18) the T-cells did not respond to HPV16 peptides (FIG. 17; HD17) and in one case no T-cells exfiltrated the tissue at all (HD13). In these 4 cases we were not able to detect circulating HPV16-specific IFNγ-producing T-cells in the post-challenge blood sample. Co-staining of the biopsy-T cells by CD4 and CD8 cell surface markers showed that not only HPV 16-specific CD4+ but also HPV16-specific CD8+ T cells infiltrated the skin site upon intradermal challenge with HPV16 peptide (FIG. 18). Overall, in 3 out of 4 biopsies infiltrated by HPV16-specific T-cells, we were able to detect HPV16-specific CD8+ T cells. The CD8+ T cells isolated from the biopsy (pool 6) of HD2 responded to both overlapping peptides of the injected skin test: HPV16 E6$_{109\text{-}140}$ and E6$_{127\text{-}158}$ (data not shown), while the CD8+ T cells of both subjects HD15 and HD16 responded to HPV16 E6$_{37\text{-}68}$ (see example for HD15, FIG. 18).

Taken together, the population of immune cells migrating into the skin upon an intradermal challenge with HPV16 peptides comprises HPV16-specific CD4+ Th1−, Th2− and CD8+ cytotoxic T cells. This infiltration is paralleled by the appearance of circulating HPV 16-specific IFNγ-producing T-cells in the blood.

Discussion

Skin tests are commonly used as a simple assay for in vivo measurement of cell mediated immunity. We have validated the use of the skin test assay for the measurement of HPV 16 specific cellular immune response against the early antigens E2, E6 and E7 in vivo by comparing the results with that of parallel measurements of T cell reactivity by in vitro assays.

In the group of healthy volunteers early skin reactions appeared between 4 to 12 days after intradermal antigen challenge. In these individuals, known to display HPV16 specific type 1 T cell responses in vitro (de Jong A et al, 2002; Welters et al, 2003), the appearance of an early skin reaction (within 13 days) was significantly associated with the detection of IFNγ-producing HPV16-specific T cells at a frequency of at least 1 per 20.000 PBMC (FIG. 15, p<0.001). The same cut-off criteria for a positive reaction in the IFNγ ELIspot assay are recommended by Jeffries et al (Jeffries D J et al, 2006), who used mathematical tools to define the appropriate cut-off of the ELISPOT in relation to Mantoux-tests. The low number of circulating memory T cells (FIG. 15) may explain why the skin reactions appear somewhat delayed compared to classical DTH tests. The T cells need to be boosted or reactivated and start to divide before enough cells are produced to cause a local inflammatory reaction: the positive skin test. Indeed, at the time a positive skin reaction appears, a higher frequency of HPV16-specific Th1 responses can be detected in the peripheral blood (FIG. 16).

Historically it has been postulated that the Th1 cell induce DTH responses, however, several studies have now shown that also Th2 cells infiltrating the skin test sites (Wang S et al, 1999; Woodfolk J A et al, 2001). Similarly, this study shows that the positive skin test sites of healthy volunteers contain both Th1 and Th2 type HPV16-specific T cells (FIGS. 17 and 18). In addition, positive skin reactions may also be the result of the influx of non-specific T cells as became evident from two in depth studies of positive skin test sites used to assay the specific immune response following vaccination of patients with renal cell cancer or melanoma (Bleumer I et al, 2007). Also this study showed that a number of positive skin test sites from healthy subjects were infiltrated with T-cells that did not respond to the injected HPV16 antigens. So far, the reason for a-specific positive skin reactions remains unclear. Unexpectedly, we observed the majority of skin reactions in healthy individuals to appear 2 to 3 weeks after intradermal injection of the antigen. While, these late positive skin reactions were not correlated with detection of circulating HPV-specific CD4+ memory T cells in pre-challenge blood (FIG. 15) the immunological constitution of these skin test sites are similar to that of classic DTH tests (Platt J L et al, 1983; Poulter L W et al, 1982) and comprised of HPV16-specific CD4+ Th1− and Th2− cells as well as HPV16-specific CD8+ T cells (FIGS. 17 and 18). We hypothesize that these reactions might be the result of T cell priming. This has also been noted in 29% of patients whom underwent a 2-step tuberculin skin testing protocol and whom were only positive at the second test round (Akcay A et al, 2003). In general, vaccine-induced T cell responses peak at 10 to 14 days after vaccination and not at three weeks. However, one should bear in mind that in such protocol a higher antigen dose as well as strong adjuvants are injected. It is therefore reasonable to assume that the T cell responses induced by intradermal challenge develop more slowly and peak at a later period. Since the intradermal peptide challenge in healthy volunteers results in the induction of both HPV 16-specific CD4+ and CD8+ T cells it, therefore, should be considered as a single, low dose vaccination. The main objective of this pilot study was to validate the use of the HPV16 specific skin test to detect type 1 immune responses in vivo. In healthy volunteers, a positive skin reaction within 13 days is indeed correlated with the presence of circulating IFNγ-producing memory T cells as detected by the IFNγ ELIspot in vitro. Importantly, we also observed discrepancies between the outcomes obtained by skin test and ELIspot. In a number of cases HPV 16-specific circulating IFNγ-producing T cells were detected in the post-challenge blood samples but without a concomitant skin reaction and vice versa (FIG. 16), and this may be considered as a false negative or false positive result. In order to fully understand the impact of this on the interpretation of the detection of type 1 immunity against HPV, we have begun a field trial in a large group of HPV positive patients and healthy volunteers in Indonesia.

TABLE 1

HLA binding and C-terminal cleavage by proteasomes of protential CTL epitopes. Table 1 discloses SEQ ID NOS 25-77, respectively, in order of appearance.

|  | Peptide Binding[1] | | Proteasomal Cleavage of C-terminus[2] | | |
|---|---|---|---|---|---|
|  |  |  | IP | IP | HH |
|  | Affinity | Stability | (RMA) | (JY) | (HeLa) |
| HLA-A*0101 | | | | | |
| 117-126 GTAKSVTCTY | intermediate | + | − | − | − |
| 196-205 RVEGNLRVEY | intermediate | + | − | − | − |

TABLE 1-continued

HLA binding and C-terminal cleavage by proteasomes of protential CTL epitopes. Table 1 discloses SEQ ID NOS 25-77, respectively, in order of appearance.

| | | Peptide Binding[1] | | Proteasomal Cleavage of C-terminus[2] | | |
|---|---|---|---|---|---|---|
| | | | | IP | IP | HH |
| | | Affinity | Stability | (RMA) | (JY) | (HeLa) |
| 205-214 | YLDDRNTFRH | intermediate | + | | | |
| 226-234 | GSDCTTIHY | high | + | + | | + |
| 229-236 | CTTIHYNY | intermediate | − | − | | − |
| **HLA-A*0201[3]** | | | | | | |
| 24-32 | KLLPENNVL | intermediate | NT | + | + | + |
| 65-73 | RMPEAAPPV | high | 6 h | − | − | − |
| 113-122 | FLHSGTAKSV | low | 6 h | + | + | + |
| 149-157 | STPPPGTRV | low | <2 h | + | + | + |
| 187-197 | GLAPPQHLIRV | high | 6 h | + | + | + |
| 264-272 | LLGRNSFEV | intermediate | 6 h | − | − | − |
| 322-330 | PLDGEYFTL | intermediate | ? | + | + | + |
| **HLA-A*0301** | | | | | | |
| 101-110 | KTYQGSYGFR | high | +/− | − | − | − |
| 110-120 | RLGFLHSGTAK | high | + | + | + | − |
| 111-120 | LGFLHSGTAK | high | +/− | + | + | − |
| 112-120 | GFLHSGTAK | intermediate | − | + | + | − |
| 113-120 | FLHSGTAK | intermediate | +/− | + | + | − |
| 117-126 | GTAKSVTCTY | intermediate | − | +/− | + | +/− |
| 122-132 | VTCTYSPALNK | intermediate | + | − | − | − |
| 124-132 | CTYSPALNK | high | + | − | − | − |
| 129-139 | ALNKMFCQLAK | high | + | + | + | + |
| 132-139 | KMFCQLAK | high | + | + | + | + |
| 154-163 | GTRVRAMAIY | intermediate | − | − | − | − |
| 154-164 | GTRVRAMAIYK | high | + | − | − | − |
| 156-163 | RVRAMAIY | intermediate | − | − | − | − |
| 156-164 | RVRAMAIYK | high | + | − | − | − |
| 172-181 | VVRRCPHHER | intermediate | + | − | − | − |
| 360-370 | GGSRAHSSHLK | intermediate | − | | | |
| 361-370 | GSRAHSSHLK | high | + | | | |
| 363-370 | RAHSSHLK | high | + | | | |
| 363-372 | RAHSSHLKSK | intermediate | +/− | | | |
| 363-373 | RAHSSHLKSKK | high | + | | | |
| 373-381 | KGQSTSRHK | intermediate | +/− | + | + | + |
| 376-386 | STSRHKKLMFK | high | +/− | − | − | − |
| **HLA-A*1101** | | | | | | |
| 101-110 | KTYQGSYGFR | high | +/− | − | − | − |
| 111-120 | LGFLHSGTAK | high | + | + | + | − |
| 112-120 | GFLHSGTAK | intermediate | − | + | + | − |
| 124-132 | CTYSPALNK | high | + | − | − | − |
| 132-139 | KMFCQLAK | high | + | + | + | + |
| 156-164 | RVRAMAIYK | high | + | − | − | − |
| 311-319 | NTSSSPQPK | high | +/− | − | − | − |
| 311-320 | NTSSSPQPKK | high | +/− | − | − | − |
| 312-319 | TSSSPQPK | high | +/− | − | − | − |
| 283-291 | RTEEENLRK | intermediate | +/− | | | |
| 363-370 | RAHSSHLK | intermediate | +/− | | | |
| 374-382 | GQSTSRHKK | intermediate | +/− | − | − | − |
| **HLA-A*2401** | | | | | | |
| 18-26 | TFSDLWKLL | high | + | + | + | + |
| 102-111 | TYQGSYGFRL | high | + | + | + | + |
| 106-113 | SYGFRLGF | high | + | + | + | + |
| 106-114 | SYGFRLGFL | high | +/− | + | + | + |
| 125-134 | TYSPALNKMF | high | + | − | − | − |
| 204-212 | EYLDDRNTF | high | + | | | |
| 340-348 | MFRELNEAL | high | +/− | − | − | − |

[1]Affinity of peptide binding is categorized as follows: good $IC_{50} < 5$ µM, intermediate $IC_{50} = 5$-15 µM, and low $IC_{50} > 15$-50 µM.
To determine the stability of the peptide-MHC complex, peptide binding was performed at 4° C. and 20° C. and $IC_{50}$ were determined.

TABLE 1-continued

HLA binding and C-terminal cleavage by proteasomes of protential CTL epitopes. Table 1 discloses SEQ ID NOS 25-77, respectively, in order of appearance.

|  | Peptide Binding[1] | | Proteasomal Cleavage of C-terminus[2] | | |
|---|---|---|---|---|---|
|  | Affinity | Stability | IP (RMA) | IP (JY) | HH (HeLa) |

[1] Stable peptides displayed $IC_{50}$ at 20° C. that deviated <2 times of the $IC_{50}$ at 4° C. Peptides that displayed $IC_{50}$ at 20° C. of more than twice the $IC_{50}$ at 4° C. but $IC_{50}$ < 15 μM were considered to bind with intermediate stability. The rest was designated as unstable peptide binding.
[2] Proteasome cleavage of C-terminus. 30 residue long peptides were digested by both mouse (RMA-cells) and human (B-LCL JY) derived immunoproteasomes (IP) and human (HeLa cells) derived household (HH) proteasomes.
[3] HLA-A*0201 binding peptides. Peptide binding capacity was previously determined by (16, 24, 25). Peptide stability

TABLE 2

Relation between peptide binding, proteasomal digestion and tolerance. Table 2 discloses SEQ ID NOS 78-86, respectively, in order of appearance.

| Sequence and HLA- Restriction of Naturally processed CTL epitopes | | | Tolerance | | Peptide Binding | | Proteasomal Cleavage of C-terminus | | |
|---|---|---|---|---|---|---|---|---|---|
| Position | Sequence | HLA- restriction | WTp53 Human | p53-/- mice | Affinity | Stability | IP (RMA) | IP (JY) | HH (HeLa) |
| P53 65-73 | RMPEAAPPV | HLA-A*0201 | NO | | high | 6 h | − | − | − |
| P53 149-157 | STPPPGTRV | HLA-A*0201 | NO | | low | <2 h | + | + | + |
| P53 187-197 | GLAPPQHLIRV | HLA-A*0201 | YES | NO | high | 6 h | + | + | + |
| P53 125-134 | TYSPALNKMF | HLA-A*2401 | NO | | high | | + | − | − |
| P53 264-272 | LLGRNSFEV | HLA-A*0201 | NO | | intermediate | 6 h | − | − | − |
| PRA 100-108 | VLDGLDVLL | HLA-A*0201 | NO | | intermediate | 2.5 h | | + | |
| PRA 142-151 | SLYSFPEPEA | HLA-A*0201 | NO | | high | 3 h | | + | |
| PRA 300-309 | ALYVDSLFFL | HLA-A*0201 | NO | | high | >4 h | | + | |
| PRA 425-433 | SLLQHLIGL | HLA-A*0201 | NO | | high | >4 h | | + | |

TABLE 3

10 p53 peptides used in the phase I/II vaccination study. Table 3 discloses SEQ ID NOS 21, 2, 3, 20, 4, 5, 15, 6, 14 and 7, respectively, in order of appearance.

| Amino acid | Sequence | Number |
|---|---|---|
| 70-99 | APPVAPAPAAPTPAAPAPAPSWPLSSSVPS | 1 |
| 86-115 | APAPSWPLSSSVPSQKTYQGSYGFRLGFLH | 2 |
| 102-131 | TYQGSYGFRLGFLHSGTAKSVTCTYSPALN | 3 |
| 126-155 | YSPALNKMFCQLAKTCPVQLWVDSTPPPGT | 4 |
| 142-171 | PVQLWVDSTPPPGTRVRAMAIYKQSQHMTE | 5 |
| 157-186 | VRAMAIYKQSQHMTEVVRRCPHHERCSDSD | 6 |
| 174-203 | RRCPHHERCSDSDGLAPPQHLIRVEGNLRV | 7 |
| 190-219 | PPQHLIRVEGNLRVEYLDDRNTFRHSVVVP | 8 |
| 206-235 | LDDRNTFRHSVVVPYEPPEVGSDCTTIHYN | 9 |
| 224-248 | EVGSDCTTIHYNYMCNSSCMGGMNR | 10 |

TABLE 4 whole vaccination and analysis process in ovarian cancer patients

| | Screening | Visit 1 Day 0 | Visit 2 Day 10 | Visit 3 Day 21 | Visit 5 Day 31 | Visit 6 Day 42 | Visit 7 Day 52 | Visit 8 Day 63 | Visit 9 Day 76 | Follow up |
|---|---|---|---|---|---|---|---|---|---|---|
| Informed consent | | | | | | | | | | |
| Study nr. | | | | | | | | | | |
| Performance status WHO | | | | | | | | | | |
| Medical examination | | | | | | | | | | |
| Physical examination | | | | | | | | | | |
| Medication | | | | | | | | | | |
| CT Scan | | | | | | | | | | Day 105-126 |
| ECG | | | | | | | | | | |
| Hematology, CA 125 & Biochemistry | | | | | | | | | | |
| Urine | | | | | | | | | | |
| PBMC collection | | | | | | | | | | |
| Punch biopsy | | | | | | | | | | |
| Vaccination | | | | | | | | | | |
| Diary | | | | | | | | | | |
| Advers events | | | | | | | | | | |
| Standard Follow up | | | | | | | | | | |

TABLE 5

Analysis of the affinity and stability of the epitopes for HLA binding as well as proteasome processing of some preferred peptides

| ISA peptide vaccine | Predicted epitopes HLA type (p53 aa) | HLA binding Affinity | Stability | Prot. Cleavage | Tolerance |
|---|---|---|---|---|---|
| p53 86-115 | A3 (101-110) | high | +/− | − | |
| | A11 (101-110) | high | +/− | − | |
| p53 102-131 | A1 (117-126) | int | + | − | |
| | A2 (113-122) | low | 6 h | + | |
| | A3 (111-120) | high | +/− | + | |
| | A3 (112-120) | int | − | + | |
| | A3 (113-120) | int | − | +/− | |
| | A3 (117-126) | int | − | +/− | |
| | A11 (112-120) | int | − | + | |
| | A24 (106-114) | high | +/− | + | |
| p53 142-171 | A2 (149-157) | low | − | + | no |
| | A3 (154-163) | int | − | − | |
| | A3 (154-164) | high | + | − | |
| | A3 (156-163) | int | − | − | |
| | A3 (156-164) | high | + | − | |
| | A11 (156-164) | high | + | − | |
| p53 157-186 | A3 (172-181) | int | + | − | |
| p53 190-219 | A1 (196-205) | int | + | − | |
| | A1 (205-214) | int | + | ? | |
| | A24 (204-212) | high | + | ? | |
| p53 224-248 | A1 (226-234) | high | + | + | |
| | A1 (229-236) | low | − | − | |
| p53 225-254 | A1 (229-236) | low | − | − | |
| p53 257-286 | A2 (264-272) | int | 6 h | − | |
| p53 273-302 | A11 (283-291) | int | +/− | ? | |
| p53 305-334 | A11 (311-319) | high | +/− | − | |
| | A11 (311-320) | high | +/− | − | |
| | A11 (312-319) | high | +/− | − | |
| p53 337-366 | A24 (340-348) | high | +/− | − | |
| p53 353-382 | A3 (360-370) | int | − | ? | |
| | A3 (361-370) | high | + | ? | |
| | A3 (363-370) | high | + | ? | |
| | A3 (363-372) | int | − | ? | |
| | A3 (363-373) | high | + | ? | |
| | A3 (373-381) | int | − | + | |
| | A11 (363-370) | int | +/− | ? | |
| p53 369-393 | A3 (376-386) | high | − | − | |
| | A11 (374-382) | int | +/− | − | |

TABLE 6

Summary of p53-specific T-cell responses of patients with colorectal cancer vaccinated twice with the p53-SLP vaccine.

| Patient | | 1-78[1] | 70-115 | 102-155 | 142-203 | 190-248 | 241-393 |
|---|---|---|---|---|---|---|---|
| 1 | ELISPOT | − | − | − | +[2] | + | − |
| | LST | − | − | + | + | + | + |
| 2 | ELISPOT | − | − | − | + | + | − |
| | LST | − | − | − | + | + | + |
| 3 | ELISPOT | − | + | − | − | − | − |
| | LST | − | − | − | − | + | − |
| 4 | ELISPOT | + | + | + | + | + | + |
| | LST | − | − | − | + | − | − |
| 5 | ELISPOT | − | − | − | − | − | − |
| | LST | − | − | − | − | − | − |
| 7 | ELISPOT | − | − | − | − | − | + |
| | LST | − | − | + | − | + | − |
| 8 | ELISPOT | − | − | + | + | + | − |
| | LST | − | − | − | − | − | − |
| 9 | ELISPOT | − | + | + | + | + | − |
| | LST | − | − | − | − | + | − |
| 10 | ELISPOT | − | − | − | − | − | − |
| | LST | − | − | + | + | + | − |
| Total positive pts | | 1 | 3 | 6 | 6 | 8 | 4 |

[1] The number of the first and last amino acid of the amino acid sequence of the p53 protein that is covered by the pool of peptides used is depicted. The columns with the first and last amino acid in bold depict the parts of the p53 protein tat are used in the vaccine.

[2] A plus-sign indicates that this patient displayed a vaccine-induced p53-specific T-cell response to this pool of p53 peptides.

TABLE 7

Cellular and humoural vaccine-induced T-cell responses and clinical responses to p53-SLP vaccine in ovarian cancer patients

| Patient | Vaccine-induced T-cell responses in PBMC (IFN-γELISPOT)[1] | Vaccine-induced T-cell responses in PBMC (proliferation assay)[2] | p53-specific T-cell responses in lymphocytes from skin biopsies[3] | p53-specific antibodies after immunisation[4] | Clinical Response CA-125[6] | CT[7] |
|---|---|---|---|---|---|---|
| P01 | + | + | + | − | PD | PD |
| P02 | + | + | + | − | SD | PD |
| P03 | + | + | − | + (4.8)[5] | SD | PD |
| P04 | na | na | na | − | na[8] | na[8] |
| P05 | − | + | + | + | PR | PD |
| P06 | − | + | − | + | SD | PD |
| P08 | + | + | + | − | PD | PD |
| P09 | − | − | − | + | SD | PD |
| P11 | + | nt | na | − | PD | PD |
| P12 | na | na | na | − | na[8] | na[8] |
| P13 | + | + | + | + (2.9) | PD | PD |
| P14 | − | − | − | − | PD | PD |
| P15 | − | − | nt | + | PD | PD |
| P17 | − | + | − | − | SD | SD |
| P18 | + | + | − | + | PD | PD |
| P19 | + | + | + | + (2.5) | PD | PD |
| P20 | − | + | nt | − | PD | PD |
| P21 | + | + | + | − | SD | PD |
| P22 | + | + | + | − | PD | PD |
| P23 | + | + | + | + | SD | SD |

[1]Vaccine-induced T cell responses after 4 immunisations as measured by IFN-γ ELISPOT. − no vaccine-induced response, + a vaccine-induced response.
[2]Vaccine-induced T-cell responses after 4 immunisations as measured by proliferation assay. − no vaccine-induced response, + a vaccine-induced response.
[3]P53-specific responses in lymphocytes cultured from skin biopsies as measured by proliferation assay. − no p53-specific T-cell reactivity, + p53-specific T-cell reactivity.
[4]Serum p53 IgG titers after immunisation as measured by quantitative ELISA. − no p53-specific antibodies, + p53-specific antibodies.
[5]The fold of vaccine-induced increase in p53-specific antibody titer.
[6]CA-125 levels evaluated according to GCIG criteria.
[7]CT scan evaluated according to RECIST criteria.
[8]Patient no evaluated by CA-125 level or CT scan due to clinically evident rapidly progressive disease.
na = not available.
nt = not terminated.

TABLE 8

N/Vaccine-induced p53-specific immune responses in PBMC of ovarian cancer patients immunised with the p53-SLP vaccine as analysed by IFN-γ ELISPOT

| Patient[1] | After one vaccination (I) | | | | After two vaccinations (II) | | | | After three vaccinations (III) | | | | After four vaccinations (IV) | | | |
|---|---|---|---|---|---|---|---|---|---|---|---|---|---|---|---|---|
| | vac p1-p2[2] | vac p3-p4 | vac p5-p7 | vac p8-p10 | vac p1-p2 | vac p3-p4 | vac p5-p7 | vac p8-p10 | vac p1-p2 | vac p3-p4 | vac p5-p7 | vac p8-p10 | vac p1-p2 | vac p3-p4 | vac p5-p7 | vac p8-p10 |
| P01 | — | 62[3] | 17 | 106 | — | 14 | — | 33 | — | — | — | — | — | 20 | — | 56 |
| P02 | — | — | — | — | — | — | — | 28 | — | — | — | 21 | — | — | 66 | 27 |
| P03 | — | 52 | 37 | 166 | — | 29 | 15 | 81 | — | 43 | 58 | 132 | — | 15 | 20 | 57 |
| P04 | — | — | — | — | — | — | — | — | na | na | na | na | na | na | na | na |
| P05 | — | 19 | 19 | 11 | — | — | — | — | — | — | 29 | 18 | — | — | — | — |
| P06 | — | 12 | 47 | 22 | — | — | — | 21 | — | — | — | — | — | — | — | — |
| P08 | 110 | 131 | 241 | 220 | 76 | 130 | 200 | 303 | 42 | 113 | 44 | 219 | — | 59 | 32 | 156 |
| P09 | — | 31 | 38 | 55 | — | 10 | 18 | 20 | — | 14 | 12 | — | — | — | — | — |
| P11 | — | 71 | 120 | 138 | — | — | 78 | — | — | — | 35 | — | — | — | 28 | — |
| P12 | 26 | — | 67 | 73 | na | na | na | na | na | na | na | na | na | na | na | na |
| P13 | — | 65 | 65 | 81 | 37 | 83 | 133 | 144 | 16 | — | 125 | 93 | — | — | 49 | 21 |
| P14 | — | 60 | — | 22 | — | — | 12 | 48 | — | — | — | — | — | — | — | — |
| P15 | — | — | 18 | — | — | 22 | 20 | — | — | — | 14 | — | — | — | — | — |
| P17 | — | 63 | 46 | 21 | — | — | 52 | 20 | — | — | — | — | — | — | — | — |
| P18 | — | 88 | 106 | 120 | — | 41 | 61 | 45 | — | — | — | 60 | — | 41 | 13 | — |
| P19 | — | — | 183 | 94 | — | — | 75 | 60 | — | — | — | — | — | — | — | 23 |
| P20 | — | — | — | 34 | — | 11 | — | 28 | — | 10 | — | 53 | — | — | — | — |
| P21 | 22 | 119 | 100 | 178 | — | 88 | 81 | 32 | — | 33 | 38 | 32 | — | 12 | 16 | — |
| P22 | 14 | 80 | 257 | 367 | 21 | 57 | 201 | 295 | — | 77 | 217 | 345 | — | — | — | 64 |
| P23 | — | 50 | 106 | 21 | — | — | 35 | — | — | 20 | 55 | 22 | — | 13 | — | — |

[1]Patients analysed for p53-specific responses before and after every immunisation (time points I-IV) by IFN-γ ELISPOT.
[2]The pool of p53 vaccine peptides used to stimulate patient-derived PBMC in vitro for 4 days.
[3]Only vaccine-induced p53-specific responses are shown (see definition in Material and Methods). Responses are depicted as number of specific spots per 10[5] PBMC (mean of experimental wells − (mean + 2 × SD) of medium control).

TABLE 8-continued

N/Vaccine-induced p53-specific immune responses in PBMC of ovarian cancer patients immunised with the p53-SLP vaccine as analysed by IFN-γ ELISPOT

| Patient[1] | After one vaccination (I) | | | | After two vaccinations (II) | | | | After three vaccinations (III) | | | | After four vaccinations (IV) | | | |
|---|---|---|---|---|---|---|---|---|---|---|---|---|---|---|---|---|
| | vac p1-p2[2] | vac p3-p4 | vac p5-p7 | vac p8-p10 | vac p1-p2 | vac p3-p4 | vac p5-p7 | vac p8-p10 | vac p1-p2 | vac p3-p4 | vac p5-p7 | vac p8-p10 | vac p1-p2 | vac p3-p4 | vac p5-p7 | vac p8-p10 |

— = no vaccine-induced p53-specific response;
na = PBMC were not available.

TABLE 9

Vaccine-induced p53-specific T-cell responses after four immunisations in freshly isolated PBMC of ovarian cancer patients immunised with the p53-SLP vaccine as analysed by proliferation assay.

| Patient[1] | Vaccine peptides | | | | Non-vaccine peptides | |
|---|---|---|---|---|---|---|
| | vac p1-p2[2] | vac p3-p4 | vac p5-p7 | vac p8-p10 | p1-p4 | p16-p24 |
| P01 | — | 13[3] | 6.8 | 6.4 | — | — |
| P02 | — | — | — | 15.8 | — | — |
| P03 | — | 24 | 14.5 | 5.3 | — | — |
| P05 | — | 3.9 | 2.5 | 3.3 | — | — |
| P06 | — | — | — | 3.4 | — | — |
| P08 | — | — | 4.4 | 7.8 | — | 4.0 |
| P09 | — | — | — | — | — | — |
| P11 | nt | nt | nt | nt | nt | nt |
| P13 | — | 2.3 | 4.9 | 3 | — | — |
| P14 | — | — | — | — | — | — |
| P15 | — | — | — | — | — | — |
| P17 | — | — | — | 7.1 | — | — |
| P18 | 2.3 | 3.1 | — | — | — | — |
| P19 | — | 16.5 | 7.4 | — | — | — |
| P20 | 3.7 | 5.1 | — | 2.4 | — | — |
| P21 | 6.9 | 25.4 | 4.6 | 8.0 | 6.4 | 5.4 |
| P22 | — | — | 67.6 | 14.0 | — | 22.3 |
| P23 | 6.4 | 3.2 | — | — | 3.6 | 2.1 |
| Total | 4 (23.5%) | 8 (47.1%) | 8 (47.1%) | 11 (64.7%) | 2 (11.8%) | 4 (23.5%) |

[1]Patients analysed for p53-specific responses before and after four immunisations by proliferation assay.
[2]The pool of p53 peptides (vaccine peptides or non-vaccine peptides) used to stimulate patient-derived PBMC in vitro for 6 days. Proliferation was measured by $^3$H-thymidine incorporation.
[3]Responses are depicted as the mean of p53-induced proliferation after four immunisations divided by the mean of p53-induced proliferation before immunisation. A response >2 was considered a vaccine-induced response. Otherwise the response was considered negative (—).
nt = not tested.

TABLE 10

Clinical Responses to p53-SLP immunotherapy after four immunisations according to serum CA-125 levels and CT scan in ovarian cancer patients.

| Patient | Target lesions[1] | Non-target lesions[1] | New Lesions[1] | CA-125[2] | Overall Best Reponse[2] |
|---|---|---|---|---|---|
| 001 | PD | | Yes | PD | PD |
| 002 | PD | | Yes | SD | PD |
| 003 | PD | PD | Yes | SD | PD |
| 004 | ND | ND | ND | ND | ND* |
| 005 | | | Yes | PR | PD |
| 006 | PD | | Yes | SD | PD |
| 008 | | | Yes | PD | PD |
| 009 | | PD | No | SD | PD |
| 011 | PD | | Yes | PD | PD |
| 012 | ND | ND | ND | ND | ND* |
| 013 | PD | PD | Yes | PD | PD |
| 014 | PD | | Yes | PD | PD |
| 015 | | | Yes | PD | PD |
| 017 | | | No | SD | SD |
| 018 | PD | | Yes | PD | PD |
| 019 | | | Yes | PD | PD |
| 020 | PD | | Yes | PD | PD |
| 021 | PD | PD | Yes | SD | PD |
| 022 | SD | | Yes | PD | PD |
| 023 | SD | | No | SD | SD |

[1]Evaluated according to RECIST criteria;
[2]Evaluated according to GCIG criteria.
PD = progressive disease;
SD = stable disease;
PR = partial response;
ND = dot done
*clinically progressive after 2 immunisations

REFERENCES LIST

Akcay, A., Erdem, Y., Altun, B., Usalan, C., Agca, E., Yasavul, U., Turgan, C., and Caglar, S. The booster phenomenon in 2-step tuberculin skin testing of patients receiving long-term hemodialysis. Am. J. Infect. Control, 31: 371-374, 2003.

Allen, P. M. Peptides in positive and negative selection: a delicate balance, Cell. 76: 593-6., 1994.

Alvarez D. et al, J. of Immunology, (2005), 174:1664-1674

Ashton-Rickardt, P. G., Bandeira, A., Delaney, J. R., Van Kaer, L., Pircher, H. P., Zinkernagel, R. M., and Tonegawa, S. Evidence for a differential avidity model of T cell selection in the thymus, Cell. 76: 651-63., 1994.

Barfoed, A. M., Petersen, T. R., Kirkin, A. F., Thor Straten, P., Claesson, M. H., and Zeuthen, J. Cytotoxic T-lymphocyte clones, established by stimulation with the HLA-A2 binding p5365-73 wild type peptide loaded on dendritic cells In vitro, specifically recognize and lyse HLA-A2 tumour cells overexpressing the p53 protein, Scand J. Immunol. 51: 128-33, 2000.

Benham, A. M., Gromme, M., and Neefjes, J. Allelic differences in the relationship between proteasome activity and MHC class I peptide loading, J. Immunol. 161: 83-9., 1998.

Bleumer, I., Tiemessen, D. M., Oosterwijk-Wakka, J. C., Voller, M. C., De Weijer, K., Mulders, P. F., and Oosterwijk, E. Preliminary analysis of patients with progressive renal cell carcinoma vaccinated with CA9-peptide-pulsed mature dendritic cells. J. Immunother., 30: 116-122, 2007.

Buckanovich R J et al, (2008), Nature Medicine 14:28-36.

Chikamatsu, K., Nakano, K., Storkus, W. J., Appella, E., Lotze, M. T., Whiteside, T. L., and DeLeo, A. B. Generation of anti-p53 cytotoxic T lymphocytes from human peripheral blood using autologous dendritic cells [In Process Citation], Clin Cancer Res. 5: 1281-8, 1999.

Dai, L. C., West, K., Littaua, R., Takahashi, K., and Ennis, F. A. Mutation of human immunodeficiency virus type 1 at amino acid 585 on gp41 results in loss of killing by CD8+ A24-restricted cytotoxic T lymphocytes, J. Virol. 66: 3151-4., 1992.

de Jong, A., van der Burg, S. H., Kwappenberg, K. M., van der Hulst, J. M., Franken, K. L., Geluk, A., van Meijgaarden, K. E., Drijfhout, J. W., Kenter, G., Vermeij, P., Melief, C. J., and Offring a, R. Frequent detection of human papillomavirus 16 E2-specific T-helper immunity in healthy subjects. Cancer Res., 62: 472-479, 2002.

de Jong, A., van der Hulst, J. M., Kenter, G. G., Drijfhout, J. W., Franken, K. L., Vermeij, P., Offring a, R., van der Burg, S. H., and Melief, C. J. Rapid enrichment of human papillomavirus (HPV)-specific polyclonal T cell populations for adoptive immunotherapy of cervical cancer. Int. J. Cancer, 114: 274-282, 2005.

de Jong, A., van Poelgeest, M. I., van der Hulst, J. M., Drijfhout, J. W., Fleuren, G. J., Melief, C. J., Kenter, G., Offring a, R., and van der Burg, S. H. Human papillomavirus type 16-positive cervical cancer is associated with impaired CD4+ T-cell immunity against early antigens E2 and E6. Cancer Res., 64: 5449-5455, 2004.

Eura, M., Chikamatsu, K., Katsura, F., Obata, A., Sobao, Y., Takiguchi, M., Song, Y., Appella, E., Whiteside, T. L., and DeLeo, A. B. A wild-type sequence p53 peptide presented by HLA-A24 induces cytotoxic T lymphocytes that recognize squamous cell carcinomas of the head and neck, Clin Cancer Res. 6: 979-86., 2000.

Ferdinanda Gabriela, Manuela Ludovisi, Giacomo Corrado, Vito Carone, Marco Petrillo and Giovanni Scambia, Prognostic role of Ca125 response criteria and RECIST criteria: Analysis of results from the MITO-3 phase III trial of gemcitabine versus pegylated doxorubicin in recurrent ovarian cancer, (2008), Gynecologic Oncology, 109: 187-193.

Geier, E., Pfeifer, G., Wilm, M., Lucchiari-Hartz, M., Baumeister, W., Eichmann, K., and Niedermann, G. A giant protease with potential to substitute for some functions of the proteasome, Science. 283: 978-81., 1999.

Glas, R., Bogyo, M., McMaster, J. S., Gaczynska, M., and Ploegh, H. L. A proteolytic system that compensates for loss of proteasome function, Nature. 392: 618-22., 1998.

Goonewardene T I, Hall M R, Rustin G J., Management of asymptomatic patients on follow-up for ovarian cancer with rising CA-125 concentrations. Lancet Oncol. (2007) 8(9):813-21.

Hernandez, J., Lee, P. P., Davis, M. M., and Sherman, L. A. The use of HLA A2.1/p53 peptide tetramers to visualize the impact of self tolerance on the TCR repertoire [In Process Citation], J. Immunol. 164: 596-602, 2000.

Hersey P, Menzies S W, Coventry B, et al. Phase I/II study of immunotherapy with T-cell peptide epitopes in patients with stage 1V melanoma. Cancer Immunol. Immunother. 2005; 54(3): 208-18.

Honda, R., Tanaka, H., and Yasuda, H. Oncoprotein MDM2 is a ubiquitin ligase E3 for tumor suppressor p53, FEBS Lett. 420: 25-7., 1997.

Hopfl, R., Heim, K., Christensen, N., Zumbach, K., Wieland, U., Volgger, B., Widschwendter, A., Haimbuchner, S., Muller-Holzner, E., Pawlita, M., Pfister, H., and Fritsch, P. Spontaneous regression of CIN and delayed-type hypersensitivity to HPV-16 oncoprotein E7. Lancet, 356: 1985-1986, 2000.

Hopfl, R., Sandbichler, M., Sepp, N., Heim, K., Muller-Holzner, E., Wartusch, B., Dapunt, O., Jochmus-Kudielka, I., ter Meulen, J., Gissmann, L., and Skin test for HPV type 16 proteins in cervical intraepithelial neoplasia. Lancet, 337: 373-374, 1991.

Houbiers, J. G., Nijman, H. W., van der Burg, S. H., Drijfhout, J. W., Kenemans, P., van de Velde, C. J., Brand, A., Momburg, F., Kast, W. M., and Melief, C. J. In vitro induction of human cytotoxic T lymphocyte responses against peptides of mutant and wild-type p53, Eur J. Immunol. 23: 2072-7, 1993.

Jeffries, D. J., Hill, P. C., Fox, A., Lugos, M., Jackson-Sillah, D. J., Adegbola, R. A., and Brookes, R. H. Identifying ELISPOT and skin test cut-offs for diagnosis of *Mycobacterium tuberculosis* infection in The Gambia. Int. J. Tuberc. Lung Dis., 10: 192-198, 2006.

Kappler, J. W., Roehm, N., and Marrack, P. T cell tolerance by clonal elimination in the thymus, Cell. 49: 273-80., 1987.

Kessler, J. H., Beekman, N. J., Bres-Vloemans, S. A., Verdijk, P., van Veelen, P. A., Kloosterman-Joosten, A. M., Vissers, D. C., ten Bosch, G. J., Kester, M. G., Sijts, A., Wouter Drijfhout, J., Ossendorp, F., Offring a, R., and Melief, C. J. Efficient identification of novel HLA-A(*)0201-presented cytotoxic T lymphocyte epitopes in the widely expressed tumor antigen PRAME by proteasome-mediated digestion analysis, J Exp Med. 193: 73-88., 2001.

Kloetzel P M & Ossendorp F Curr Opin Immunol. 2004 February; 16(1):76-81.

Luckey, C. J., Marto, J. A., Partridge, M., Hall, E., White, F. M., Lippolis, J. D., Shabanowitz, J., Hunt, D. F., and Engelhard, V. H. Differences in the expression of human class I MHC alleles and their associated peptides in the presence of proteasome inhibitors, J. Immunol. 167: 1212-21., 2001.

Luckey, C. J., King, G. M., Marto, J. A., Venketeswaran, S., Maier, B. F., Crotzer, V. L., Colella, T. A., Shabanowitz, J., Hunt, D. F., and Engelhard, V. H. Proteasomes can either generate or destroy MHC class I epitopes: evidence for nonproteasomal epitope generation in the cytosol, Journal of Immunology J1-JI. 161: 112-121, 1998.

Macagno, A., Gilliet, M., Sallusto, F., Lanzavecchia, A., Nestle, F. 0., and Groettrup, M. Dendritic cells up-regulate immunoproteasomes and the proteasome regulator PA28 during maturation, Eur J. Immunol. 29: 4037-42, 1999.

Mayordomo, J. I., Loftus, D. J., Sakamoto, H., De Cesare, C. M., Appasamy, P. M., Lotze, M. T., Storkus, W. J., Appella, E., and DeLeo, A. B. Therapy of murine tumors with p53 wild-type and mutant sequence peptide-based vaccines, J Exp Med. 183: 1357-65, 1996.

Milner, J. Different forms of p53 detected by monoclonal antibodies in non-dividing and dividing lymphocytes, Nature. 310: 143-5., 1984.

Morel, S., Levy, F., Burlet-Schiltz, 0., Brasseur, F., Probst-Kepper, M., Peitrequin, A. L., Monsarrat, B., Van Velthoven, R., Cerottini, J. C., Boon, T., Gairin, J. E., and Van den Eynde, B. J. Processing of some antigens by the standard proteasome but not by the immunoproteasome results in poor presentation by dendritic cells, Immunity. 12: 107-17, 2000.

Momand, J., Zambetti, G. P., Olson, D. C., George, D., and Levine, A. J. The mdm-2 oncogene product forms a complex with the p53 protein and inhibits p53-mediated transactivation, Cell. 69: 1237-45., 1992.

Morgan et al. Science. 2006 Oct. 6; 314(5796):126-9.

Nijman, H. W., Houbiers, J. G., van der Burg, S. H., Vierboom, M. P., Kenemans, P., Kast, W. M., and Melief, C. J. Characterization of cytotoxic T lymphocyte epitopes of a self-protein, p53, and a non-self-protein, influenza matrix:

relationship between major histocompatibility complex peptide binding affinity and immune responsiveness to peptides, J Immunother. 14: 121-6, 1993.

Platt, J. L., Grant, B. W., Eddy, A. A., and Michael, A. F. Immune cell populations in cutaneous delayed-type hypersensitivity. J. Exp. Med., 158: 1227-1242, 1983.

Poulter, L. W., Seymour, G. J., Duke, 0., Janossy, G., and Panayi, G. Immunohistological analysis of delayed-type hypersensitivity in man. Cell Immunol., 74: 358-369, 1982.

Rammensee, H. G., Friede, T., and Stevanoviic, S. MHC ligands and peptide motifs: first listing, Immunogenetics. 41: 178-228, 1995.

Reimann, J. and Schirmbeck, R. Alternative pathways for processing exogenous and endogenous antigens that can generate peptides for MHC class I-restricted presentation, Immunol Rev. 172: 131-52., 1999.

Rogel, A., Popliker, M., Webb, C. G., and Oren, M. p53 cellular tumor antigen: analysis of mRNA levels in normal adult tissues, embryos, and tumors, Mol Cell Biol. 5: 2851-5., 1985.

Romani N. et al, Springer Semin Immunopathol., (1992), 13:265-279.

Ropke, M., Hald, J., Guldberg, P., Zeuthen, J., Norgaard, L., Fugger, L., Svejgaard, A., Van der Burg, S., Nijman, H. W., Melief, C. J., and Claesson, M. H. Spontaneous human squamous cell carcinomas are killed by a human cytotoxic T lymphocyte clone recognizing a wild-type p53-derived peptide, Proc Natl Acad Sci USA. 93: 14704-7, 1996.

Rosenberg S A, Yang J C, Schwartzentruber D J, et al. Immunologic and therapeutic evaluation of a synthetic peptide vaccine for the treatment of patients with metastatic melanoma. Nat. Med. 1998; 4(3):321-7.

Rustin G J, Bast R C Jr, Kelloff G J, Barrett J C, Carter S K, Nisen P D, Sigman C C, Parkinson D R, Ruddon R W, Use of CA-125 in clinical trial evaluation of new therapeutic drugs for ovarian cancer. Clin Cancer Res. 2004; 10:3919-26.

Sebzda, E., Wallace, V. A., Mayer, J., Yeung, R. S., Mak, T. W., and Ohashi, P. S. Positive and negative thymocyte selection induced by different concentrations of a single peptide, Science. 263: 1615-8., 1994.

Sette, A., Sidney, J., del Guercio, M. F., Southwood, S., Ruppert, J., Dahlberg, C., Grey, H. M., and Kubo, R. T. Peptide binding to the most frequent HLA-A class I alleles measured by quantitative molecular binding assays, Mol. Immunol. 31: 813-22., 1994.

Shkedy, D., Gonen, H., Bercovich, B., and Ciechanover, A. Complete reconstitution of conjugation and subsequent degradation of the tumor suppressor protein p53 by purified components of the ubiquitin proteolytic system, FEBS Lett. 348: 126-30., 1994.

Stohwasser, R., Standera, S., Peters, I., Kloetzel, P. M., and Groettrup, M. Molecular cloning of the mouse proteasome subunits MC14 and MECL-1: reciprocally regulated tissue expression of interferon-gamma-modulated proteasome subunits, Eur J. Immunol. 27: 1182-7., 1997.

Terada, N., Lucas, J. J., and Gelfand, E. W. Differential regulation of the tumor suppressor molecules, retinoblastoma susceptibility gene product (Rb) and p53, during cell cycle progression of normal human T cells, J. Immunol. 147: 698-704., 1991.

Therasse P, Arbuck S G, Eisenhauer E A, et al. New guidelines to evaluate the response to treatment in solid tumors. European Organization for Research and Treatment of Cancer, National Cancer Institute of the United States, National Cancer Institute of Canada. J. Natl. Cancer Inst. 2000; 92(3):205-16.

Theobald M & Offring a R. Expert Rev Mol. Med. 2003 Mar. 28; 2003:1-13.

Theobald, M., Biggs, J., Dittmer, D., Levine, A. J., and Sherman, L. A. Targeting p53 as a general tumor antigen, Proc Natl Acad Sci USA. 92: 11993-7., 1995.

Theobald, M., Biggs, J., Hernandez, J., Lustgarten, J., Labadie, C., and Sherman, L. A. Tolerance to p53 by A2.1-restricted cytotoxic T lymphocytes, J Exp Med. 185: 833-41, 1997.

Theobald, M., Ruppert, T., Kuckelkorn, U., Hernandez, J., Haussler, A., Ferreira, E. A., Liewer, U., Biggs, J., Levine, A. J., Huber, C., Koszinowski, U. H., Kloetzel, P. M., and Sherman, L. A. The sequence alteration associated with a mutational hotspot in p53 protects cells from lysis by cytotoxic T lymphocytes specific for a flanking peptide epitope, J Exp Med. 188: 1017-28, 1998.

Tilkin, A. F., Lubin, R., Soussi, T., Lazar, V., Janin, N., Mathieu, M. C., Lefrere, I., Carlu, C., Roy, M., Kayibanda, M., and et al. Primary proliferative T cell response to wild-type p53 protein in patients with breast cancer, Eur J. Immunol. 25: 1765-9, 1995.

van der Burg, S. H., Ras, E., Drijfhout, J. W., Benckhuijsen, W. E., Bremers, A. J., Melief, C. J., and Kast, W. M. An HLA class I peptide-binding assay based on competition for binding to class 1 molecules on intact human B cells. Identification of conserved HIV-1 polymerase peptides binding to HLA-A*0301, Hum Immunol. 44: 189-98, 1995.

van der Burg, S. H., Visseren, M. J., Brandt, R. M., Kast, W. M., and Melief, C. J. Immunogenicity of peptides bound to MHC class I molecules depends on the MHC-peptide complex stability, J. Immunol. 156: 3308-14, 1996.

van der Burg, S. H., Kwappenberg, K. M., Geluk, A., van der, K. M., Pontesilli, 0., Hovenkamp, E., Franken, K. L., van Meijgaarden, K. E., Drijfhout, J. W., Ottenhoff, T. H., Melief, C. J., and Offring a, R. Identification of a conserved universal Th epitope in HIV-1 reverse transcriptase that is processed and presented to HIV-specific $CD4^+$ T cells by at least four unrelated HLA-DR molecules. J. Immunol., 162: 152-160, 1999.

van der Burg, S. H., Ressing, M. E., Kwappenberg, K. M., de Jong, A., Straathof, K., de Jong, J., Geluk, A., van Meijgaarden, K. E., Franken, K. L., Ottenhoff, T. H., Fleuren, G. J., Kenter, G., Melief, C. J., and Offring a, R. Natural T-helper immunity against human papillomavirus type 16 (HPV16) E7-derived peptide epitopes in patients with HPV 16-positive cervical lesions: identification of 3 human leukocyte antigen class II-restricted epitopes. Int. J. Cancer, 91: 612-618, 2001.

van der Burg, S. H., de Cock, K., Menon, A. G., Franken, K. L., Palmen, M., Redeker, A., Drijfhout, J., Kuppen, P. J., van de Velde, C., Erdile, L., Tollenaar, R. A., Melief, C. J., and Offring a, R. Long lasting p53-specific T cell memory responses in the absence of anti-p53 antibodies in patients with resected primary colorectal cancer, Eur J. Immunol. 31: 146-55., 2001.

Vierboom, M. P., Zwaveling, S., Bos, G. M. J., Ooms, M., Krietemeijer, G. M., Melief, C. J., and Offring a, R. High steady-state levels of p53 are not a prerequisite for tumor eradication by wild-type p53-specific cytotoxic T lymphocytes, Cancer Res. 60: 5508-13., 2000.

Wang, S., Fan, Y., Brunham, R. C., and Yang, X. IFN-gamma knockout mice show Th2-associated delayed-type hypersensitivity and the inflammatory cells fail to localize and control chlamydial infection. Eur. J. Immunol., 29: 3782-3792, 1999.

Welters, M. J., de Jong, A., van den Eeden, S. J., van der Hulst, J. M., Kwappenberg, K. M., Hassane, S., Franken, K. L., Drijfhout, J. W., Fleuren, G. J., Kenter, G., Melief, C. J., Offring a, R., and van der Burg, S. H. Frequent display of human papillomavirus type 16 E6-specific memory t-Helper cells in the healthy population as witness of previous viral encounter. Cancer Res, 63: 636-641, 2003.

Woodfolk, J. A. and Platts-Mills, T. A. Diversity of the human allergen-specific T cell repertoire associated with distinct skin test reactions: delayed-type hypersensitivity-associated major epitopes induce Th1- and Th2-dominated responses. J. Immunol., 167: 5412-5419, 2001.

Zanelli, E., Zhou, P., Cao, H., Smart, M. K., and David, C. S. Genomic organization and tissue expression of the mouse proteasome gene Lmp-7, Immunogenetics. 38: 400-7, 1993

The invention claimed is:

1. A peptide composition comprising:
   i) a peptide consisting of between 22 to 45 amino acids comprising between 22 to 30 contiguous amino acids from the amino acid sequence set forth in SEQ ID NO: 4,
   ii) a peptide consisting of between 22 to 45 amino acids, comprising between 22 to 30 contiguous amino acids from the amino acid sequence set forth in SEQ ID NO: 5, and
   iii) a peptide consisting of between 22 to 45 amino acids, comprising between 22 to 30 contiguous amino acids from the amino acid sequence set forth in SEQ ID NO: 15.

2. The peptide composition of claim 1, further comprising a peptide consisting of between 22 to 45 amino acids, comprising between 22 to 30 contiguous amino acids from the amino acid sequence set forth in SEQ ID NO: 2, or a peptide consisting of between 22 to 45 amino acids, comprising between 22 to 30 contiguous amino acids from the amino acid sequence set forth in SEQ ID NO: 20.

3. A peptide composition according to claim 1, comprising:
   i) a peptide consisting of between 22 to 45 contiguous p53 amino acids, comprising between 22 to 30 contiguous amino acids from the amino acid sequence set forth in SEQ ID NO: 4,
   ii) a peptide consisting of between 22 to 45 contiguous p53 amino acids, comprising between 22 to 30 contiguous amino acids from the amino acid sequence set forth in SEQ ID NO: 5; and
   iii) a peptide consisting of between 22 to 45 contiguous p53 amino acids, comprising between 22 to 30 contiguous amino acids from the amino acid sequence set forth in SEQ ID NO: 15.

4. The peptide composition of claim 1, 2, or 3 further comprising a pharmaceutical excipient or an immune modulator.

5. The peptide composition according to claim 2, further comprising a peptide consisting of between 22 to 45 contiguous p53 amino acids, comprising between 22 to 30 contiguous amino acids from the amino acid sequence set forth in SEQ ID NO: 2, or a peptide consisting of between 22 to 45 contiguous p53 amino acids, comprising between 22 to 30 contiguous amino acids from the amino acid sequence set forth in SEQ ID NO: 20.

* * * * *